(12) United States Patent
Meliniotis et al.

(10) Patent No.: US 12,214,121 B2
(45) Date of Patent: Feb. 4, 2025

(54) DRY POWDER INHALER

(71) Applicant: VECTURA DELIVERY DEVICES LIMITED, Wiltshire (GB)

(72) Inventors: Andreas Meliniotis, Cambridgeshire (GB); Roger Clarke, Cambridgeshire (GB)

(73) Assignee: VECTURA DELIVERY DEVICES LIMITED (GB)

( * ) Notice: Subject to any disclaimer, the term of this patent is extended or adjusted under 35 U.S.C. 154(b) by 947 days.

(21) Appl. No.: 17/276,398

(22) PCT Filed: Sep. 16, 2019

(86) PCT No.: PCT/EP2019/074737
§ 371 (c)(1),
(2) Date: Mar. 15, 2021

(87) PCT Pub. No.: WO2020/058206
PCT Pub. Date: Mar. 26, 2020

(65) Prior Publication Data
US 2022/0040420 A1    Feb. 10, 2022

(30) Foreign Application Priority Data

Sep. 17, 2018 (EP) ..................................... 18194962
Dec. 3, 2018 (EP) ..................................... 18209763

(51) Int. Cl.
*A61M 15/00* (2006.01)

(52) U.S. Cl.
CPC .... *A61M 15/0051* (2014.02); *A61M 15/0025* (2014.02); *A61M 15/0026* (2014.02); *A61M 15/007* (2014.02); *A61M 2202/064* (2013.01)

(58) Field of Classification Search
CPC .............. A61M 15/00; A61M 15/0001; A61M 15/0028; A61M 15/003; A61M 15/0033;
(Continued)

(56) References Cited

U.S. PATENT DOCUMENTS

| 7,434,354 B2 * | 10/2008 | Yokomori | E05F 15/646 192/114 R |
| 2002/0053344 A1 * | 5/2002 | Davies | A61M 15/0045 128/203.15 |

(Continued)

FOREIGN PATENT DOCUMENTS

| WO | WO 2009/092652 A1 | 7/2009 |
| WO | WO 2013/175177 A1 | 11/2013 |

OTHER PUBLICATIONS

European Search Report from corresponding European Application No. 18209763.4, mailed May 27, 2019.
(Continued)

*Primary Examiner* — Timothy A Stanis
*Assistant Examiner* — Nicholas B. Engel
(74) *Attorney, Agent, or Firm* — Davidson Kappel LLC

(57) ABSTRACT

The present invention provides an inhaler comprising a housing which contains a blister strip having a plurality of blisters which contain powdered medicament for inhalation; a mouthpiece through which the medicament is inhaled by a user; an indexing wheel for indexing the blister strip; an opening mechanism for opening the blisters; an actuator which is movable between a first position and a second position in order to operate the indexing wheel and the opening mechanism; and a coupling mechanism for coupling the actuator to the indexing wheel so that the indexing wheel rotates together with the actuator during part of the motion of the actuator; characterized in that the coupling mechanism comprises a shuttle that rotates on the same axis as, and translates axially relative to, the indexing wheel.

16 Claims, 20 Drawing Sheets

(58) Field of Classification Search
CPC ......... A61M 15/0035; A61M 15/0038; A61M 15/004; A61M 15/0041; A61M 15/0045; A61M 15/0046; A61M 15/0051; A61M 2202/064; F16D 11/02; F16D 11/04; F16D 11/14; F16D 13/02; F16D 13/22; F16D 13/24; F16D 13/38; F16D 23/12; F16D 2023/123; F16D 43/26
See application file for complete search history.

(56) References Cited

U.S. PATENT DOCUMENTS

| | | | | |
|---|---|---|---|---|
| 2003/0172927 A1* | 9/2003 | Young | B65D 75/327 | 128/203.15 |
| 2004/0244794 A1* | 12/2004 | Richards | A61M 15/0043 | 128/203.15 |
| 2004/0250812 A1* | 12/2004 | Davies | A61M 15/0021 | 128/200.14 |
| 2005/0228341 A1* | 10/2005 | Edgerley | A61M 15/0066 | 604/59 |
| 2007/0137645 A1* | 6/2007 | Eason | A61M 15/0025 | 128/203.15 |
| 2008/0163868 A1* | 7/2008 | Pocock | A61M 15/0041 | 128/200.22 |
| 2009/0007908 A1* | 1/2009 | Eason | A61M 15/0058 | 128/203.15 |
| 2009/0090362 A1* | 4/2009 | Harmer | A61M 15/0045 | 128/203.21 |
| 2010/0139654 A1* | 6/2010 | Thoemmes | A61M 15/0036 | 128/203.15 |
| 2010/0288278 A1* | 11/2010 | Pocock | A61M 15/0045 | 128/203.12 |
| 2011/0030683 A1* | 2/2011 | Eason | A61M 15/0045 | 128/203.21 |
| 2011/0041841 A1* | 2/2011 | Wachtel | A61M 15/0081 | 128/203.21 |
| 2011/0048419 A1* | 3/2011 | Kirniak | A61M 15/0036 | 128/203.15 |
| 2011/0048420 A1* | 3/2011 | Gibbins | A61M 15/0045 | 128/203.21 |
| 2011/0056494 A1* | 3/2011 | Gibbins | A61M 15/0041 | 242/160.4 |
| 2011/0094507 A1* | 4/2011 | Wachtel | A61M 15/0051 | 128/200.21 |
| 2011/0094510 A1* | 4/2011 | Gibbins | A61M 15/0051 | 128/203.21 |
| 2011/0114088 A1* | 5/2011 | Eason | A61M 15/0036 | 128/200.21 |
| 2011/0120466 A1* | 5/2011 | Fagot | A61M 15/0051 | 128/203.15 |
| 2011/0120467 A1* | 5/2011 | Pardonge | A61M 15/0008 | 128/203.15 |
| 2011/0126827 A1* | 6/2011 | Kaemper | A61M 15/0051 | 128/200.23 |
| 2011/0168178 A1* | 7/2011 | Baillet | A61M 11/002 | 128/203.15 |
| 2011/0192397 A1* | 8/2011 | Saskar | A61M 15/0051 | 128/200.17 |
| 2011/0226244 A1* | 9/2011 | Perkins | A61M 15/0045 | 128/203.15 |
| 2011/0277753 A1* | 11/2011 | Dunne | A61M 15/0043 | 128/200.14 |
| 2012/0037157 A1* | 2/2012 | Rohrschneider | A61M 15/0026 | 128/203.15 |
| 2012/0037158 A1* | 2/2012 | Wachtel | A61M 15/0021 | 128/203.21 |
| 2012/0037718 A1* | 2/2012 | Dunne | A61M 11/001 | 239/1 |
| 2012/0048269 A1* | 3/2012 | Pardonge | A61M 15/0008 | 128/203.14 |
| 2012/0048270 A1* | 3/2012 | Pardonge | A61M 15/0096 | 128/203.15 |
| 2012/0097161 A1* | 4/2012 | Keegstra | A61M 15/0051 | 128/203.15 |
| 2012/0097162 A1* | 4/2012 | Keegstra | A61M 15/0043 | 128/203.15 |
| 2012/0132203 A1* | 5/2012 | Hodson | A61M 15/0065 | 128/203.15 |
| 2012/0132205 A1* | 5/2012 | Meliniotis | A61M 15/0058 | 128/203.21 |
| 2012/0138055 A1* | 6/2012 | Meliniotis | A61M 15/0045 | 128/203.15 |
| 2012/0152245 A1* | 6/2012 | Rolfs | A61M 15/0046 | 128/203.15 |
| 2012/0167881 A1* | 7/2012 | Keegstra | A61M 15/0045 | 128/203.15 |
| 2013/0133652 A1* | 5/2013 | Pardonge | A61M 15/0026 | 128/203.15 |
| 2013/0152928 A1* | 6/2013 | Kirniak | A61M 15/0051 | 128/203.15 |
| 2014/0290653 A1* | 10/2014 | Colomb | A61M 15/0008 | 128/203.15 |
| 2015/0083129 A1* | 3/2015 | Colomb | A61M 15/0091 | 128/203.15 |
| 2015/0090262 A1* | 4/2015 | Glusker | A61M 15/0055 | 128/203.15 |
| 2015/0096563 A1* | 4/2015 | Toksoz | A61M 15/0026 | 128/203.15 |
| 2015/0107590 A1* | 4/2015 | Colomb | A61M 15/0021 | 128/203.15 |
| 2015/0136128 A1* | 5/2015 | Toksoz | A61M 15/0021 | 128/202.27 |
| 2015/0151059 A1* | 6/2015 | Meliniotis | A61M 15/0021 | 128/203.15 |
| 2015/0174345 A1* | 6/2015 | Toksoz | A61M 15/0051 | 128/203.15 |
| 2015/0297841 A1* | 10/2015 | Ono | A61M 15/0055 | 128/203.15 |
| 2015/0335833 A1* | 11/2015 | Wilson | A61M 15/004 | 128/203.15 |
| 2016/0193433 A1* | 7/2016 | Thoemmes | A61M 15/0035 | 128/203.15 |
| 2016/0287818 A1* | 10/2016 | Colomb | A61M 15/0051 | |
| 2017/0016489 A1* | 1/2017 | Grosskopf | F16D 23/12 | |
| 2018/0106302 A1* | 4/2018 | Campbell | F16D 17/00 | |
| 2018/0214647 A1* | 8/2018 | Meliniotis | A61M 15/0055 | |

OTHER PUBLICATIONS

International Search Report from corresponding International Application No. PCT/EP2019/074737, mailed Nov. 27, 2019.
Written Opinion of the International Searching Authority issued on Nov. 27, 2019, from corresponding International Application No. PCT/EP2019/074737.

* cited by examiner

DRY POWDER INHALER

This application is a U.S. national phase application under 35 U.S.C. of § 371 of International Application No. PCT/EP2019/074737, Sep. 16, 2019, which claims priority of European Patent Application No. EP 18194962.9, filed Sep. 17, 2018, and European Patent Application No. EP 18209763.4, filed Dec. 3, 2018, the disclosures of which are hereby incorporated by reference herein.

TECHNICAL FIELD OF THE INVENTION

The present invention relates to a dry powder inhaler with a blister strip containing doses of medicament for inhalation.

BACKGROUND TO THE INVENTION

Inhalers provide an attractive method for administering medicaments, for example to treat local diseases of the airway or to deliver drugs to the bloodstream via the lungs. The medicament is commonly provided as a dry powder pre-packaged in individual doses, such as capsules or blisters. It is advantageous for the inhaler to hold a number of doses so that there is no need to insert a dose into the device each time it is used. Therefore, many inhalers include means for storing a number of doses, e.g. in the form of a blister strip, together with a mechanism for driving and indexing the blister strip. Such devices are disclosed in, for example, WO 05/037353, WO 09/092652 and WO13/175177.

The inhalers disclosed in WO 05/037353 have a housing containing a blister strip and a drive mechanism that includes an indexing wheel. The blister strip passes over the indexing wheel and the wheel rotates in response to pivotal movement of an actuator so as to drive the strip through the device. The actuator may be a lever or it may alternatively be the outer cover ("cap") of the inhaler. The drive mechanism is configured such that the indexing wheel rotates in response to rotation of the actuator in one direction but remains stationary when the actuator is rotated in the opposite direction, during which the blister is pierced.

WO 09/092652 discloses an inhaler having a drive mechanism in which the indexing wheel rotates to index the blister strip during the first part of the movement of the actuator in one direction, so that an unopened blister is driven into alignment with the piercer. The actuator is then disengaged from the indexing wheel so that no further rotation of the indexing wheel occurs and the blister strip is stationary. This is achieved by a drive coupling which is caused to rotate by the actuator and which engages and disengages with the indexing wheel. The drive coupling has a resilient, flexible portion which has a wedge-shaped drive dog that faces the indexing wheel. During the first part of the movement of the actuator, the flexible portion comes into contact with a barrier on the housing which deflects it towards the indexing wheel. This causes the drive dog to engage with the indexing wheel so that the indexing wheel is rotated by the drive coupling. At the end of first part of the movement of the actuator, the flexible portion passes the end of the barrier. The resilience of the flexible portion causes it to return to its undeflected position, so that the drive dog moves away from the indexing wheel and disengages from it. Thus when the drive coupling is rotated further during the second part of the motion of the actuator, the indexing wheel is not driven. The second part of the movement of the actuator causes the piercer to pierce the stationary, aligned blister. After inhalation, the user returns the actuator to its initial position. The drive coupling rotates back in the opposite direction and now passes along the other side of the barrier so that the flexible flange portion is deflected away from the indexing wheel. This enables the drive coupling to rotate in the opposite direction without driving the indexing wheel.

BRIEF DESCRIPTION OF THE INVENTION

The present invention concerns an inhaler of the same general type, but having a different mechanism by which the actuator engages and disengages with the indexing wheel. In a first aspect, the invention provides an inhaler comprising:
- a housing which contains a blister strip having a plurality of blisters which contain powdered medicament for inhalation,
- a mouthpiece through which the medicament is inhaled by a user,
- an indexing wheel for indexing the blister strip and an opening mechanism for opening the blisters,
- an actuator which is movable between a first position and a second position in order to operate the indexing wheel and the opening mechanism,
- a coupling mechanism for coupling the actuator to the indexing wheel so that the indexing wheel rotates together with the actuator during part of the motion of the actuator, characterized in that the coupling mechanism comprises a shuttle that rotates on the same axis as, and translates axially relative to, the indexing wheel.

Preferably the shuttle has a track follower which interacts with a track formation on the housing to cause the shuttle to translate axially so that it engages with the indexing wheel during a first part of the motion of the actuator.

In one embodiment, the shuttle comprises a first shuttle part and a second shuttle part. Each shuttle part preferably has a ramp follower which interacts with ramps on the housing to cause the shuttle to translate axially so that it disengages from the indexing wheel during a second part of the motion of the actuator. Preferably also, the first and second shuttle parts together form a bearing surface on which the indexing wheel is mounted for rotation.

In one embodiment, the blister strip is stationary during motion of the actuator from the second position back to the first position. Preferably the inhaler comprises an actuator gear which is connected to and driven by the actuator, the actuator gear drives the first shuttle part, and the first and second shuttle parts are connected so that rotation of the first shuttle part causes the second shuttle part to rotate.

In another embodiment, the blister strip is indexed forwards during motion of the actuator from the second position to the first position. Preferably, the inhaler comprises first and second actuator gears which are connected to and driven by the actuator, and an idler gear; and the first and second shuttle parts are axially linked together whilst being free to rotate independently of each other, wherein the first actuator gear drives the first shuttle part, and the second actuator gear drives the idler gear which in turn drives the second shuttle part, so that the first and second shuttle parts rotate in opposite senses during motion of the actuator.

More preferably, the first shuttle part drives the indexing wheel during at least part of the forward motion of the actuator from the first position to the second position, and does not drive the indexing wheel during the reverse motion of the actuator from the second position to the first position; and the second shuttle part drives the indexing wheel during at least part of the reverse motion of the actuator, and does not drive the indexing wheel during the forward motion of the actuator.

Even more preferably, the blister strip is indexed by one blister during the motion of the actuator from the first position to the second position and by another blister during the motion of the actuator from the second position to the first position, so that two blisters, which preferably contain different medicaments, are indexed and opened each time the actuator is moved from the first position to the second position and back.

In any of the embodiments, the opening mechanism may comprise a piercer; the indexing wheel indexes the blister strip during a first part of the motion of the actuator from the first position to the second position, and the piercer pierces one or more aligned blisters during a second part of the motion of the actuator from the first position to the second position.

The inhaler preferably has an outer cover which is pivotally mounted on the housing.

In one embodiment, the outer cover forms the actuator so that motion of the outer cover causes indexing of the blister strip and opening of the blisters. Preferably in the first position the outer cover is closed so that the mouthpiece is covered, and in the second position the outer cover is open so that the mouthpiece is exposed.

In an alternative embodiment, the inhaler has a lever which forms the actuator so that motion of the lever causes indexing of the blister strip and opening of the blisters.

BRIEF DESCRIPTION OF THE FIGURES

The invention will now be further described with reference to the Figures, wherein.

DETAILED DESCRIPTION OF THE INVENTION

Figure 1A:
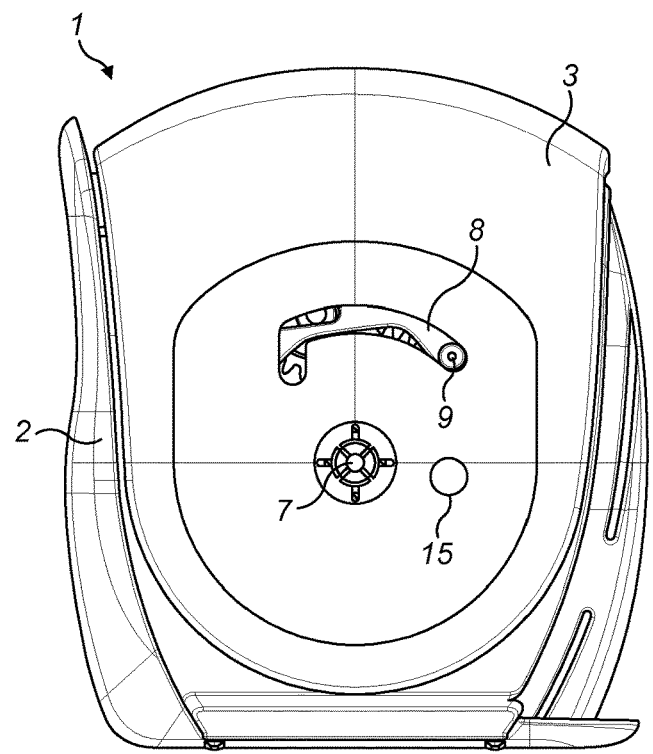
FIGS. 1A and 1B show an inhaler of the invention with the outer cover in the closed and opened positions respectively.
Figure 1B:
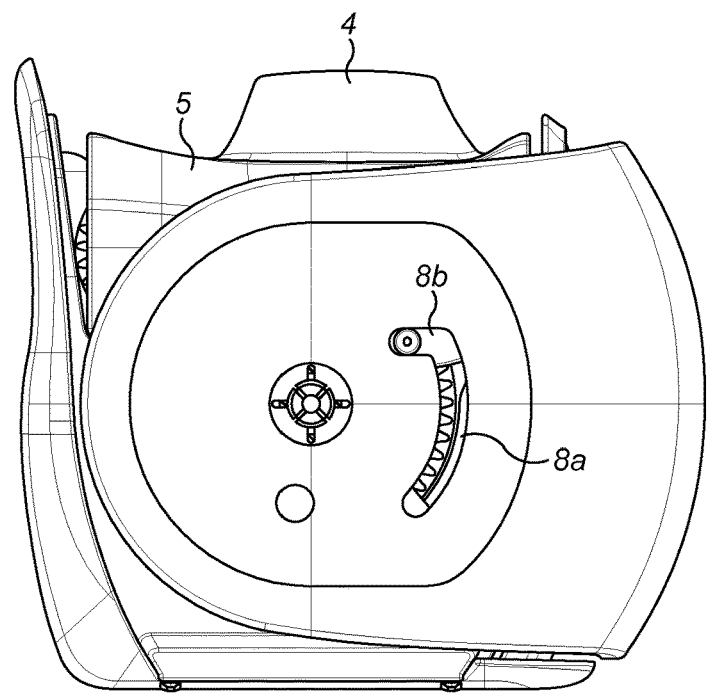

FIG. 1 shows an inhaler according to the invention. The inhaler 1 has a housing 2 formed from two shell portions 2a, 2b and an outer cover (or cap) 3. The outer cover is pivotally mounted to the housing. The outer cover 3 can be rotated through approximately 90° from a closed position as shown in FIG. 1A in which the outer cover 3 covers and protects a mouthpiece 4 to a fully open position, shown in FIG. 1B in which the mouthpiece 4 is exposed to enable a user to inhale a dose of medicament.

The inhaler contains a blister strip (not visible in FIG. 1) having a number of blisters—typically 30 or 60—which contain individual doses of medicament. The blister strip is typically cold-formed from a ductile foil laminate or a plastic material and includes a pierceable lid, typically foil or a foil laminate, which is heat-sealed around the periphery of the blister after the dose of medicament has been introduced during manufacture.

Figure 1C:
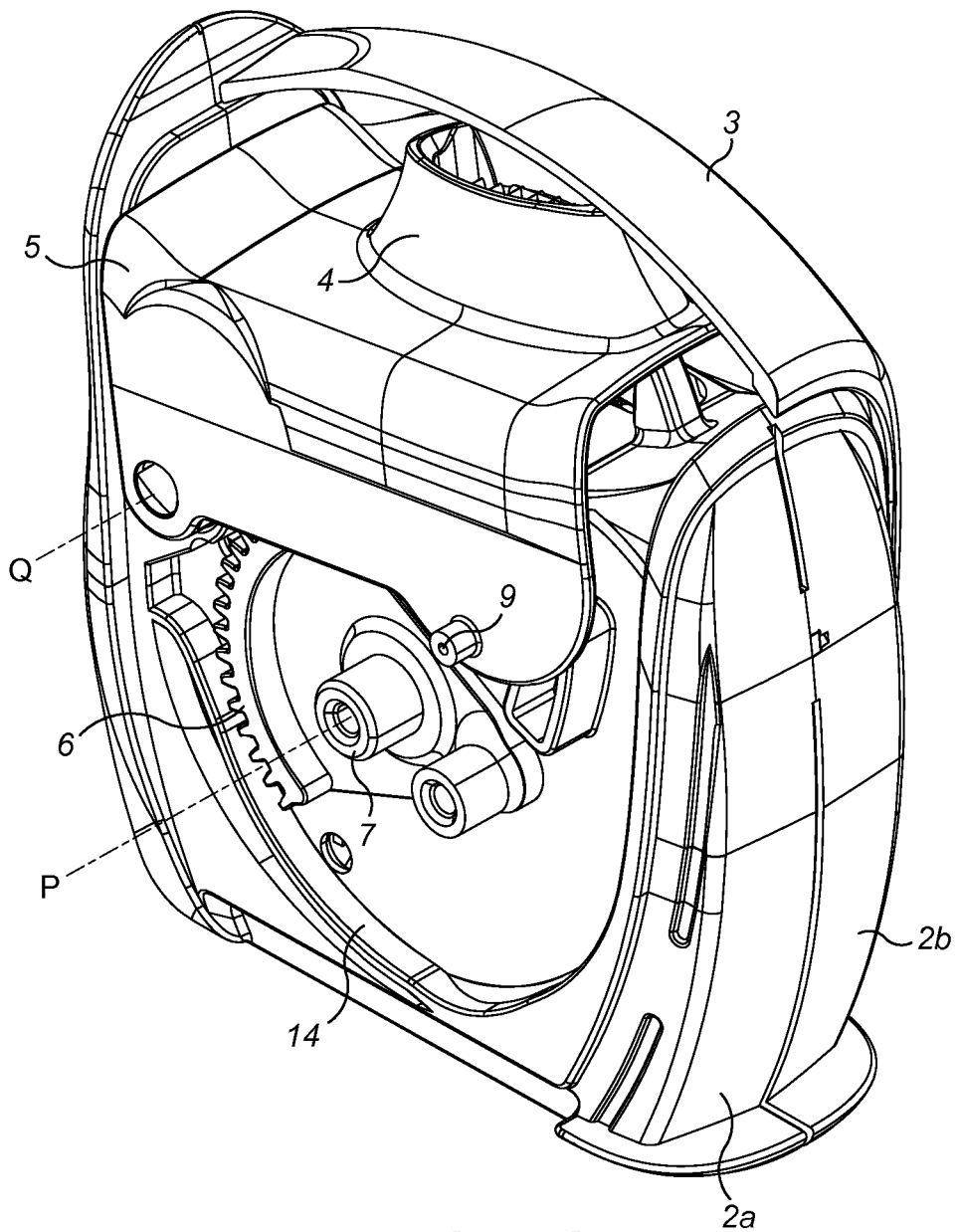
FIG. 1C shows the inhaler with one side of the outer cover removed so that the internal components are visible.

FIG. 1C shows the inhaler with the outer cover 3 partially cut away so that some of the internal components can be seen. The outer cover is mounted for rotation on axles 7 located on axis P on either side of the housing. The mouthpiece 4 is attached to or formed as part of a mouthpiece support member 5 which is pivotally mounted to the housing about a second axis Q. A piercer (not visible in FIG. 1) is located on the underside of the mouthpiece support member 5 directly beneath the mouthpiece 4. A cam 9 is located on one side of the mouthpiece support member 5 and cooperates with a cam slot 8 in the outer cover 3 to cause the mouthpiece support member and the piercer to pivot in a manner which is described in WO13/175177. Alternatively, the mouthpiece support member could be fixed to the housing, and the piercer may be pivotally mounted to the mouthpiece support member so that the piercer pivots relative to the mouthpiece.

The inhaler has an indexing mechanism 6 (only part of which is visible) that selectively couples the outer cover to a blister strip indexing wheel in a manner which is explained below. Pivoting the outer cover between the closed and open positions causes the indexing wheel to index the blister strip, i.e. to sequentially move blister(s) into alignment with the piercer, and also causes the piercer to pierce the aligned blister(s). The user then inhales through the mouthpiece, which aerosolizes the powder in the pierced blister(s).

Indexing takes place during the first part of the opening movement (or "stroke"), e.g. as the outer cover is pivoted from 0 to 60°. When the outer cover is rotated beyond this point through the second part of the opening stroke, e.g. as the outer cover is pivoted from 60 to 90°, the indexing mechanism is disengaged, and the piercer pivots so that the piercing elements pierce the aligned and now stationary blister.

As the outer cover is closed, the piercing elements are withdrawn from the pierced blisters in the first part of the closing stroke, e.g. as the outer cover is pivoted from 90 to 60°. The blister strip may remain stationary or may be indexed again in the second part of the closing stroke, e.g. as the outer cover is pivoted from 60 to 0°.

Figure 2:
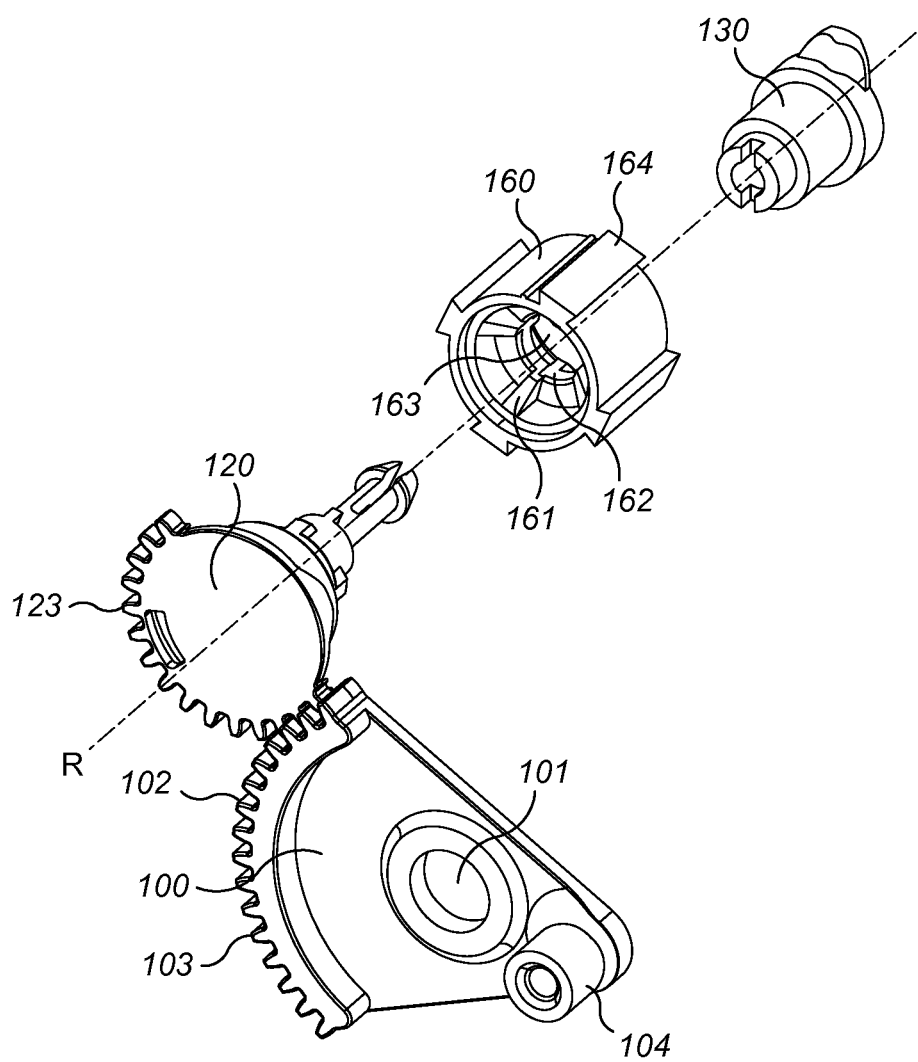
FIG. 2 shows an expanded view of the indexing mechanism of a first embodiment.

FIG. 2 shows an expanded view of the indexing mechanism of a first embodiment of an inhaler according to the invention. The mechanism comprises an actuator gear 100, a first shuttle part 120 and a second shuttle part 130 which together form a shuttle, and a blister strip indexing wheel 160.

The actuator gear 100 is formed as a plate-like portion, having a central pivot hole 101 which fits onto the axle 7 (see FIG. 1C) on the housing, so that the actuator gear is mounted for rotation about the same axis P as the outer cover. The actuator gear 100 has a gear element 102 formed from gear teeth 103 extending for approximately 90°.

The actuator gear 100 may be keyed or otherwise attached to the outer cover when the inhaler is assembled so that the actuator gear and the outer cover rotate together. For example, a round post 104 protrudes from the actuator gear and is received in a corresponding hole 15 in the outer cover 3 (shown in FIG. 1A). Opening or closing the outer cover thereby causes the actuator gear 100 to rotate about axis P. Alternatively, the actuator gear and the outer cover may be formed as a single component, for example they may be moulded together as a unitary piece.

The shuttle parts 120, 130 are mounted for rotation about a third axis R, and the indexing wheel 160 is mounted for rotation on the shuttle, also about axis R, as described below.

The actuator gear teeth 103 mesh with corresponding gear teeth 123 on the first shuttle part 120 and thereby transmit drive so that the first shuttle part 120 rotates in response to rotation of the actuator gear 100 which itself is driven by rotation of the outer cover.

The indexing wheel 160 comprises a number of spokes 161 (typically four) extending from a hub 162 which surrounds a central circular hole 163. The spokes are arranged so that a blister locates between the protruding ends 164 of successive spokes as the blister strip passes around the indexing wheel.

In contrast to WO 09/092652, the mechanism does not have a flexible drive coupling. Instead, the shuttle engages and disengages with the indexing wheel in a different manner.

Figure 3A:
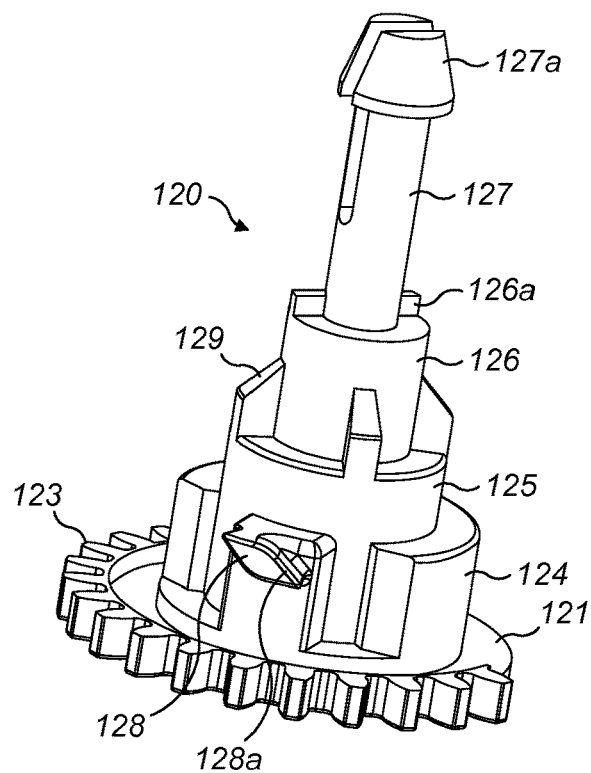
FIGS. 3A and 3B show perspective views of the first shuttle part.
Figure 3B:
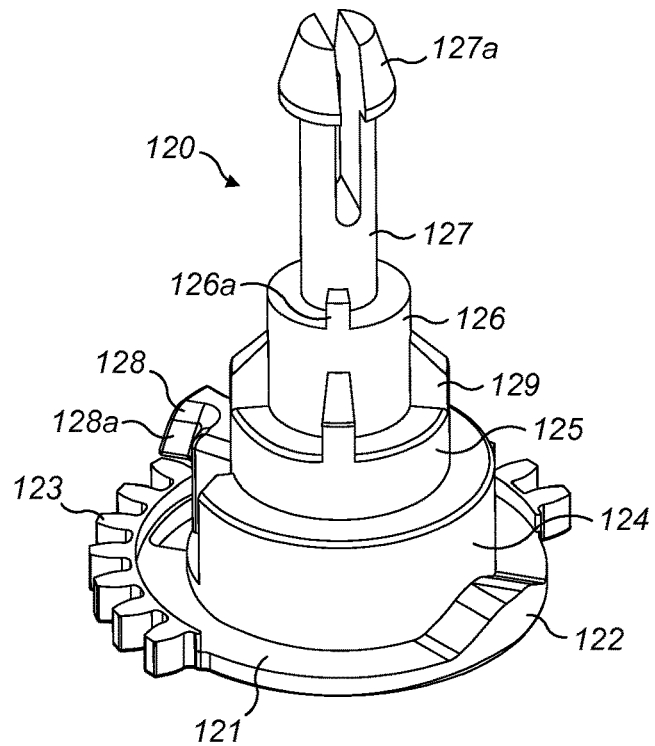

FIGS. 3A and 3B show perspective views of the first shuttle part from two different angles. The first shuttle part 120 comprises a flange 121 having a small hump on one side which functions as a first ramp follower 122, and a shaft which extends axially from the centre of the flange 121. The gear teeth 123 protrude radially from the flange around about half of its circumference on the side opposite the hump. The shaft has first, second, third and fourth cylindrical sections 124, 125, 126, 127 having different radii. The first shaft section 124, which has the largest radius, is adjacent to the flange. The fourth shaft section 127, which is furthest from the flange, has the smallest radius. The second 125 and third 126 shaft sections lie between the first 124 and fourth 127 shaft sections, and have intermediate radii. A track follower 128 protrudes radially from close to the distal end of the first shaft section 124, on the opposite side to the hump 122. Part of the first shaft section is cut away on either side of the track follower. The track follower has first and second angled engaging faces 128a, 128b on its ends, so that it is rhomboid in shape (when viewed in the radial direction).

Four equi-angularly spaced drive dogs 129 protrude radially outwards from the third shaft section 126. The drive dogs 129 are formed as walls which extend axially from the second shaft section 125 along part of the third shaft section 126. The drive dogs engage and disengage with the spokes 161 of the indexing wheel in a manner which is described below. The axial ends of both the drive dogs and the spokes are sloped at an angle of 45°. This maximizes the contact area between the faces of the drive dogs and the spokes when they are engaged, for the fixed axial engagement distance which is limited by the distance that the shuttle translates, as will be described below. A diametric rib 126a protrudes axially from the end of the third shaft section 126. A clip connection 127a is situated at the distal end of the fourth shaft section 127.

Figure 4:
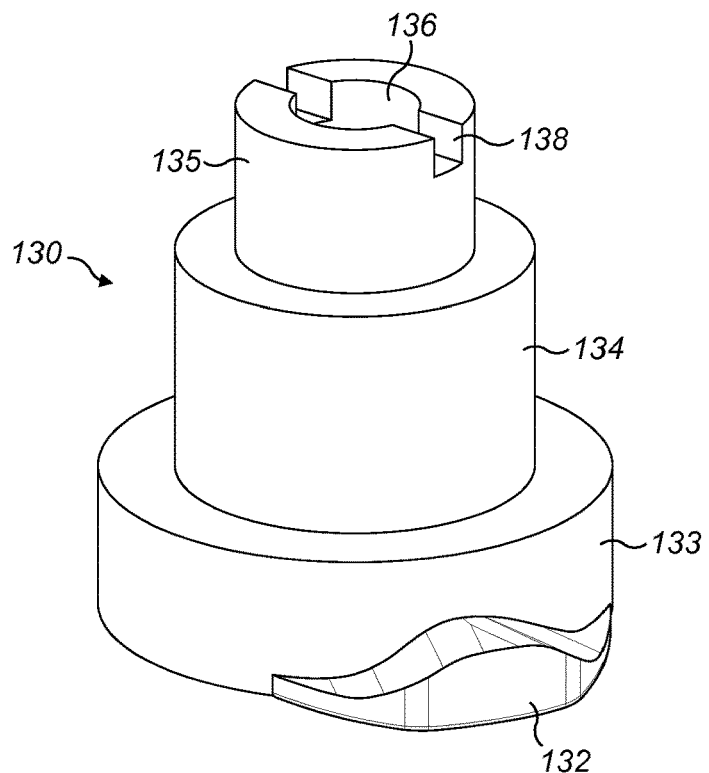
FIG. 4 shows a perspective view of the second shuttle part.

FIG. 4 shows a perspective view of the second shuttle part 130. The second shuttle part 130 has first, second and third cylindrical sections 133, 134, 135. A hump protrudes from the first cylindrical section. This functions as a second ramp follower 132. The second 134 and third 135 sections have the same radii as the second 125 and third 126 shaft sections respectively of the first shuttle part 120. A central circular hole 136 extends through the second shuttle part 130. At the end of the third section 135 there is a diametric slot 138.

Figure 5:
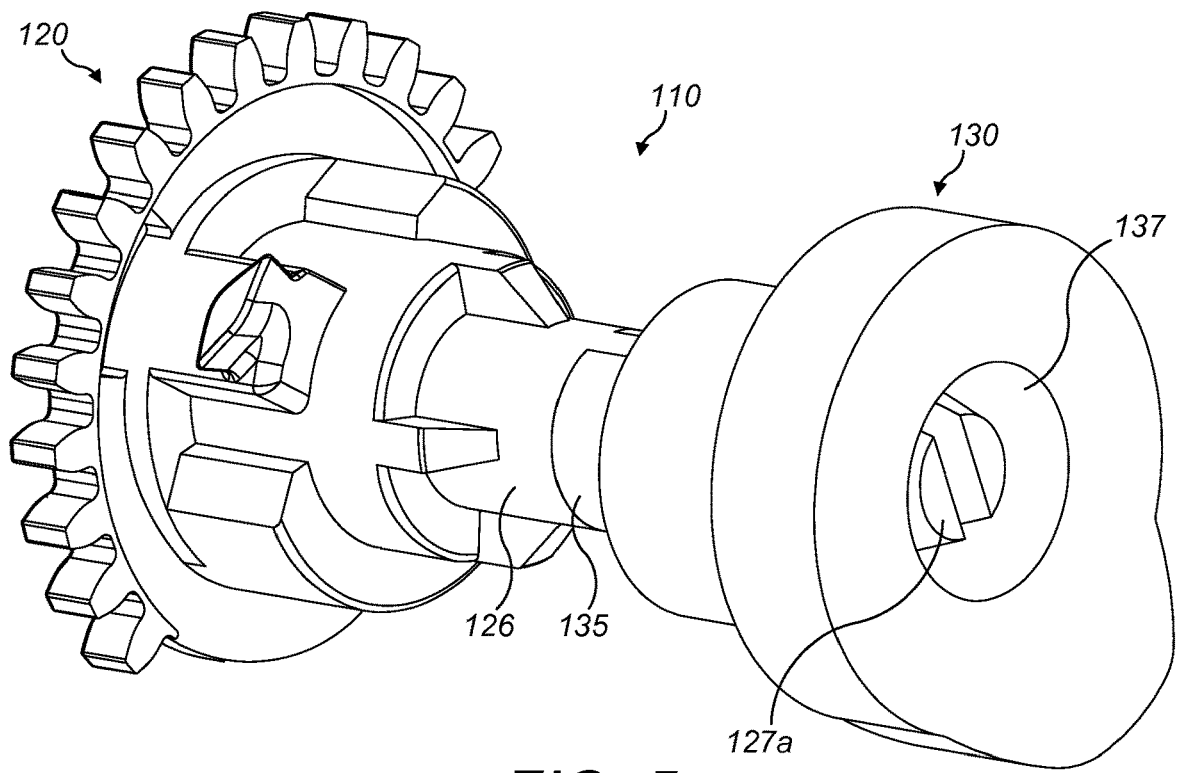
FIG. 5 shows a perspective view of the first and second shuttle parts connected together.

FIG. 5 shows the first 120 and second 130 shuttle parts assembled together to form the shuttle 110. The fourth shaft section 127 of the first shuttle part has a radius which corresponds to that of the central circular hole 136 of the second shuttle part 130. The clip connection 127a fits into a corresponding circular recess 137 on the outer side of the second shuttle part 130, thereby holding the first 120 and second 130 shuttle parts together in the axial direction. The rib 126a on the first shuttle part fits into the corresponding slot 138 on the second shuttle part so that they rotate together. The length of the fourth shaft section 127 (including the clip connection 127a) corresponds to the total thickness of the second shuttle part 130. Thus, when the fourth shaft section 127 is inserted into the central circular hole 136, the third shaft section 126 of the first shuttle part 120 abuts the third section 135 of the second shuttle part 130.

The radius of the third shaft section 126 of the first shuttle part and of the third section 135 of the second shuttle part correspond to that of the central circular hole 163 of the indexing wheel 160. These sections 126, 135 abut each other and together form a bearing surface on which the indexing wheel 160 rotates, on axis R.

Figure 6A:
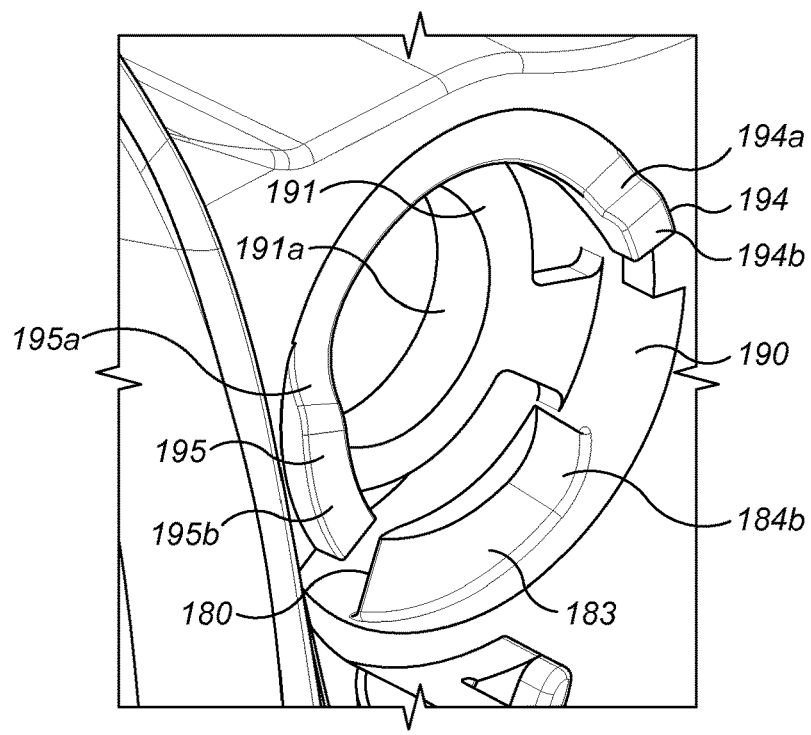
FIGS. 6A and 6B are perspective views of each side of the housing, showing the track formation and ramps.
Figure 6B:
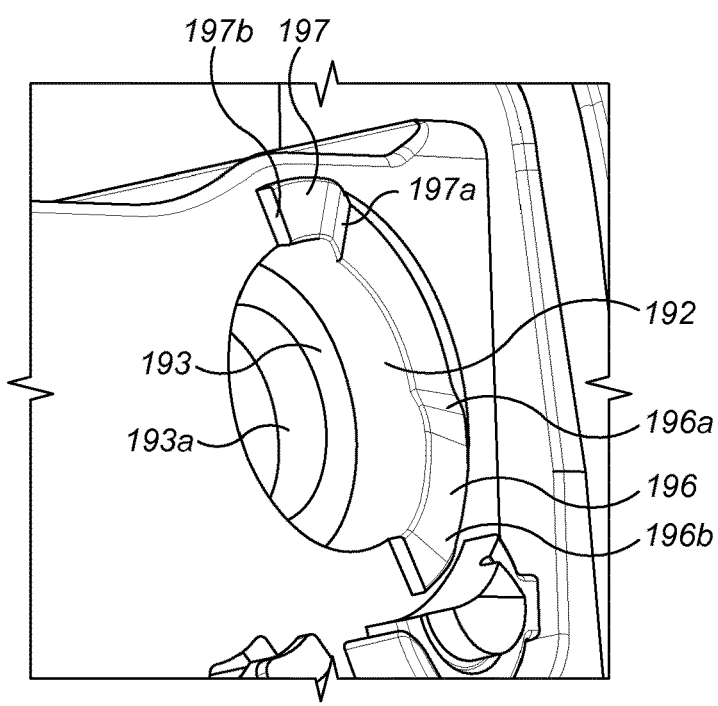
Figure 7A:
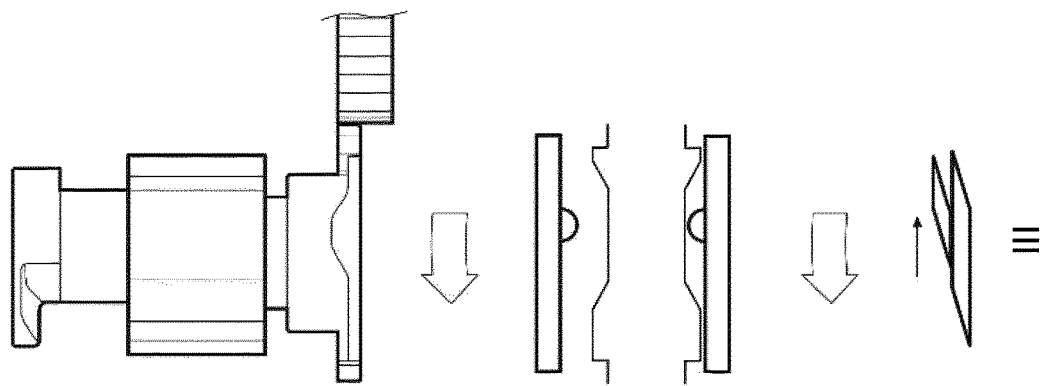
FIGS. 7A and 7B schematically show the positions of the shuttle and the indexing wheel (top row), the ramps and ramp followers (middle row) and the track follower and the track formation (bottom row) and at several stages during opening and closing of the outer cover.
Figure 7A:
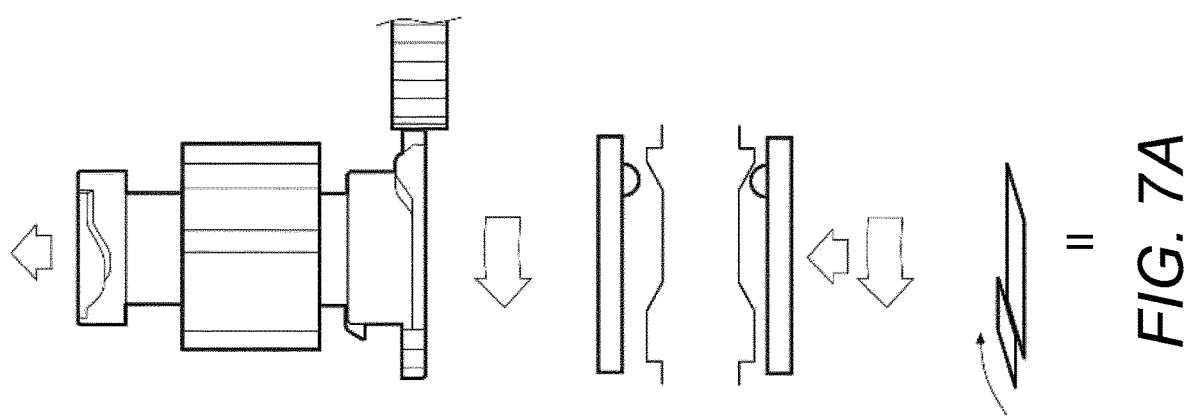
Figure 7A:
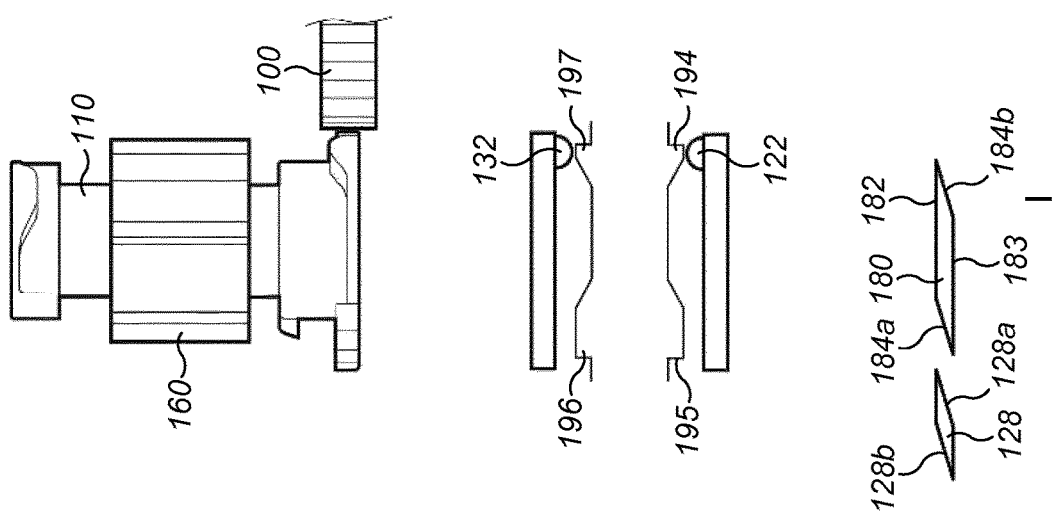
Figure 7A:
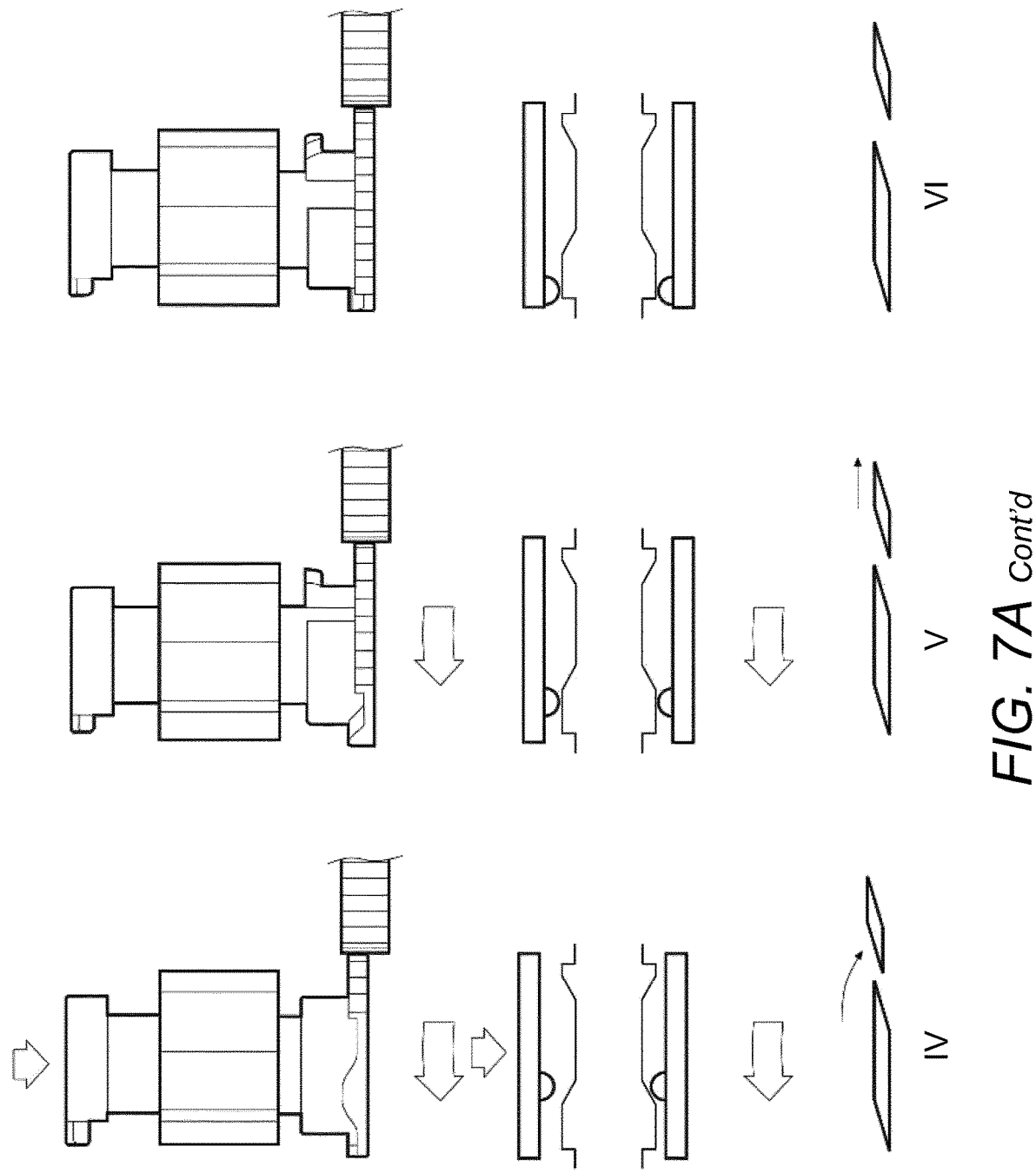
Figure 7B:
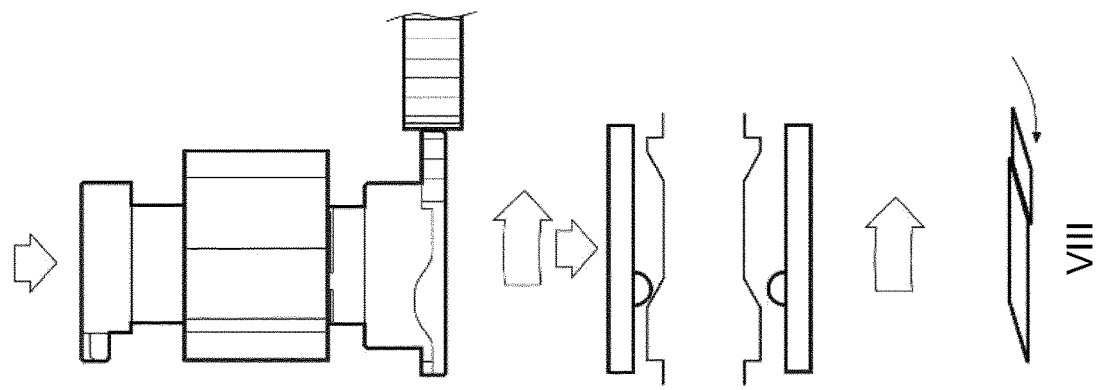
Figure 7B:
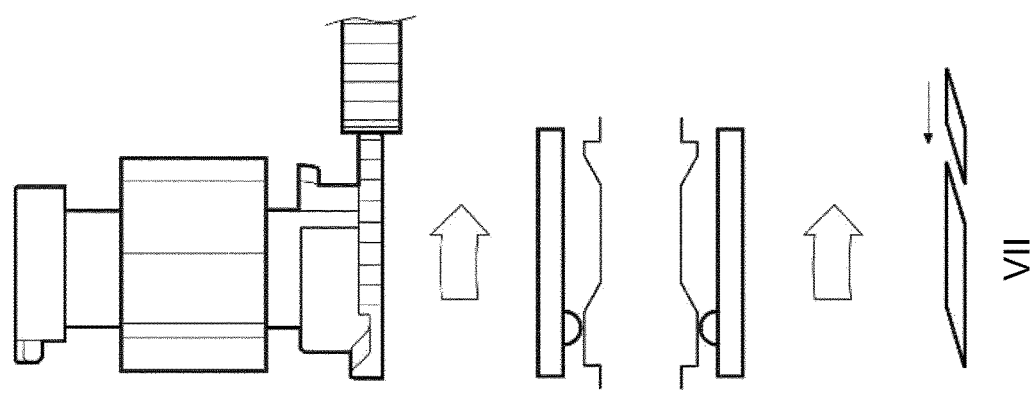
Figure 7B:
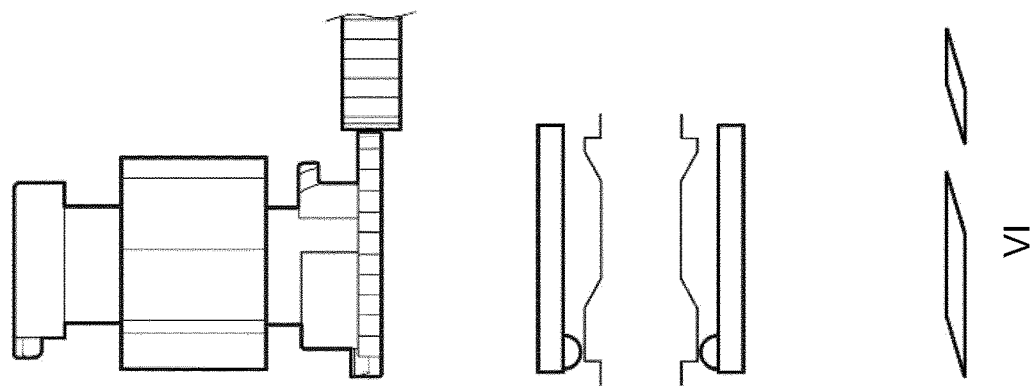
Figure 7B:
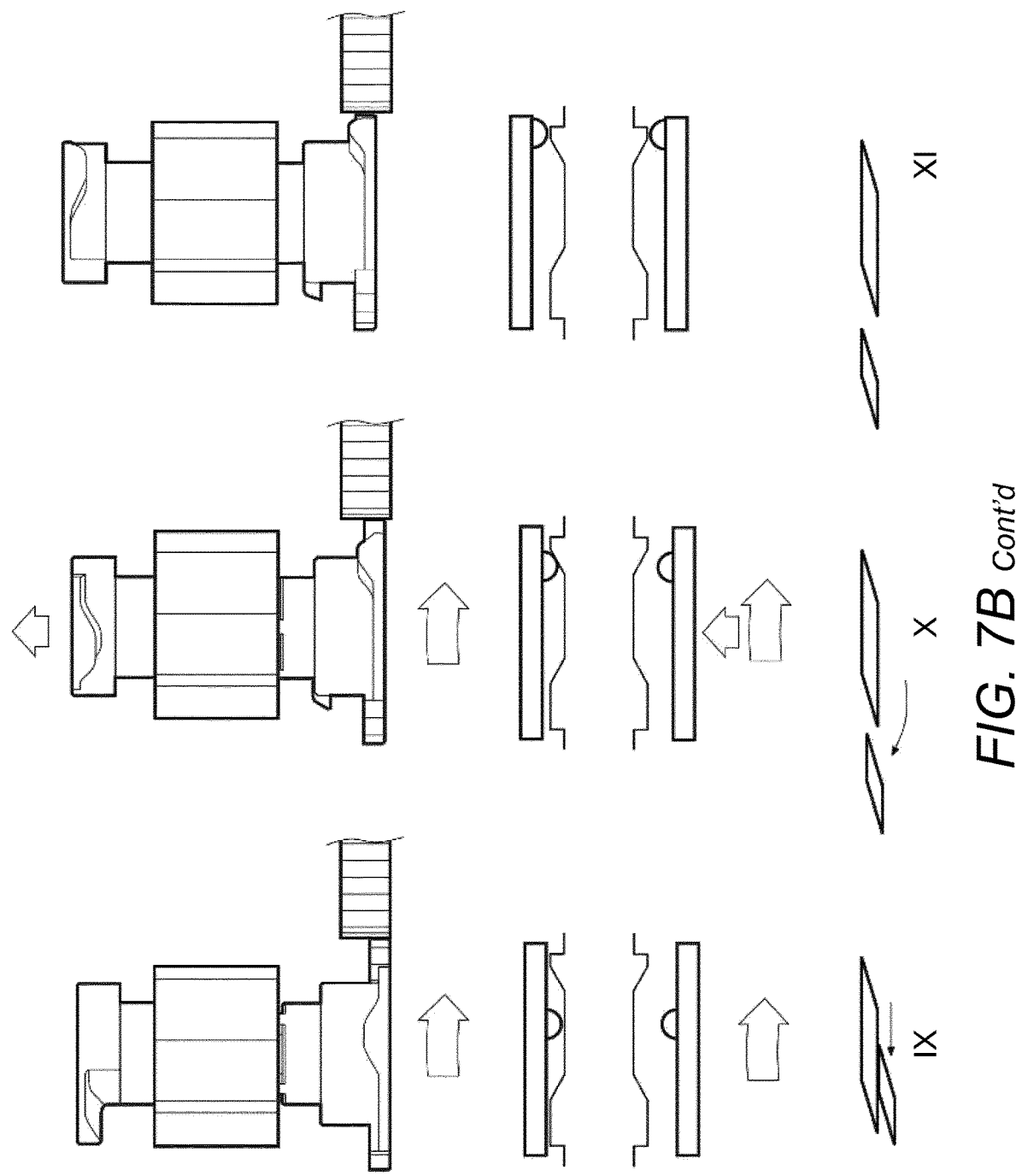

FIGS. 6A and 6B show close up views of the regions of the first (front) and second (rear) sides of the housing. The first side of the housing has a first circular recess 190 within which there is a first ring 191. Correspondingly, the second side of the housing has a second circular recess 192 and a second ring 193.

The radius of each ring 191, 193 corresponds to that of the second shaft section 125 of the first shuttle part and the second section 134 of the second shuttle part. The radially inward surface 191a of the first ring 191 forms a bearing surface for the second shaft section 125 of the first shuttle part. Similarly, the corresponding surface 193a of the second ring 193 forms a bearing surface for the second section 134 of the second shuttle part. The shuttle is thereby mounted for rotation about axis R. The indexing wheel 160 is mounted for rotation about axis R on the bearing surface formed by the third shaft section 126 of the first shuttle part 120 and the third section 135 of the second shuttle part 130. At the same time, it is held in place axially in the housing between the axial inner faces of the rings 191, 193 (these faces are not visible in FIGS. 6A and 6B).

As shown in FIG. 6A, a track formation 180 protrudes from the first circular recess 190, in the form of a barrier which defines first and second tracks 182, 183 on its opposite sides, in the same way as in WO 09/092652. The ends of the barrier have angled faces 184a, 184b. Two ramps, a short close ramp 194 and a long pierce ramp 195, protrude from the outer side of the housing adjacent to the circular recess 190 on opposite sides.

The second side of the housing has similar close and pierce ramps 197, 196 but does not have a track formation. The ramps correspond in size and shape to ramps 194, 195, but are located at different angular positions around the second circular recess 192.

The track formation 180 on the first circular recess 190 and the track follower 128 on the first shuttle part 120 operate in a similar manner to WO 09/092652, but with some differences.

Firstly, unlike WO 09/092652, there is no flexible portion that is deflected to cause engagement with the indexing wheel 160. Instead, the shuttle 110 translates axially with respect to the indexing wheel 160 along axis R so that the drive dogs 129 engage with the spokes 161. The shuttle is able to translate axially because the second shaft section 125 of the first shuttle part and the second section 134 of the second shuttle part can slide axially along the bearing surfaces 191*a*, 193*a*. The distance that the shuttle translates is equal to the width of the track formation 180 plus the width of the track follower 128. The absence of flexible parts has the advantage that the mechanism is robust and simple to manufacture.

Secondly, in order for the gear teeth on the first shuttle part to remain engaged with the actuator gear teeth when the shuttle translates, one of the sets of teeth is thicker. As shown in FIG. 2, the gear teeth 103 of the actuator gear 100 are thicker (axially) than the gear teeth 123 of the first shuttle part 120 (however, the thicker and thinner teeth could equally be the other way around). In order to ensure that the gears are fully engaged in both drive positions, the thickness of the thicker gear is thickness of the thin gear plus the axial distance that the shuttle translates.

The third difference is the mechanism by which return to the neutral (non-driving) position is achieved. In WO 09/092652, the resilience of the flexible portion causes it to spring back to its undeflected position once the track follower has passed the central barrier. In contrast, in this embodiment of the invention, return to the neutral position is achieved by the ramps and ramp followers, as follows.

FIG. 7 shows the positions of the actuator gear 100, the shuttle 110 and the indexing wheel 160 (top row), the ramps 194, 195, 196, 197 and ramp followers 122, 132 (middle row) and the track follower 128 and the track formation 180 (bottom row) at several stages during opening (FIG. 7A) and closing (FIG. 7B) of the outer cover. The track follower and ramp followers each move in a circular arc as the gears are rotated, but in FIG. 7, the motion is schematically shown as being linear for simplicity.

In stage I, the outer cover is in the closed position. The shuttle is located centrally with respect to the indexing wheel so that the drive dogs on the first shuttle part are spaced apart from the spokes, i.e. the mechanism is in neutral. Stages II, III and IV correspond to the first part of the opening stroke. The shuttle moves axially relative to the indexing wheel in a manner that is described in detail below, so that the drive dogs engage with the spokes of the indexing wheel. Stage V is the second part of the opening stroke in which the drive dogs disengage from the indexing wheel and the mechanism is in neutral whilst the piercer is inserted into the blister. In stage VI, the outer cover is in the fully open position. Stage VII is the first part of the closing stroke in which the mechanism remains in neutral whilst the piercing elements are removed. Stages VIII, IX and X correspond to the second part of the closing stroke. The shuttle translates axially in the opposite direction and the drive dogs remain disengaged from the indexing wheel. Finally, at the end of the closing stroke, the shuttle returns to the central position and the cover is in the fully closed position of stage I.

The mechanism operates as follows. When the outer case is in the closed position (stage I), the drive dogs 129 (which are not visible in FIG. 7 because they are hidden by the indexing wheel) are spaced apart from the spokes 161. The track follower 128 on the first shuttle part 120 is spaced apart from the track formation 180. The ramp followers 122, 132 sit on the tops of their respective close (short) ramps 194, 197.

When the outer cover is opened, the actuator gear rotates, causing the shuttle to rotate. The track follower 128 moves towards the track formation 180, so that the first angled engaging face 128*a* on the track follower comes into contact with the first angled engaging face 184*a* of the track formation 180. The track follower 128 rides up the angled engaging face 184*a* (stage II) towards one side 182 of the track formation. This pushes the first shuttle part 120 towards the indexing wheel 160. At the same time, the ramp follower 122 moves along the sloping section 194*a* of the first close ramp 194. The second shuttle part (which is connected to the first shuttle part by the clip connection) correspondingly moves away from the indexing wheel, and its ramp follower 132 moves clear of its close ramp 197. As a result of the axial translation of the first shuttle part, the drive dogs 129 engage the spokes 161 of the indexing wheel 160. Consequently, as the track follower 128 moves along the first track 182 (stage III), the first shuttle part 120 drives the indexing wheel 160 to rotate.

At the point when the track follower 128 reaches the end of the track formation 180 (stage IV), the ramp follower 122 on the first shuttle part comes into contact with its pierce ramp 195. Further rotation of the outer cover, and hence the shuttle, causes the ramp follower 122 to ride up the sloped section 195*a* of the pierce ramp 195. This pulls the shuttle back in the opposite direction to that in which it moved in Stage II, so that the drive dogs 129 disengage from the spokes 161 of the indexing wheel. The first ramp follower 122 reaches the flat section 195*b* of the pierce ramp, at which point the shuttle has returned to the central, neutral position. At the same time, the ramp follower 132 on the second shuttle part comes into contact with the flat section 196*b* of the pierce ramp 196 on the second (rear) side of the housing. This contact prevents the shuttle from overshooting the central position. This is the end of the first part of the opening stroke.

The length of the track formation 180 controls the extent of rotation of the indexing wheel 160 relative to the extent of rotation of the shuttle 110. The length is chosen so that the indexing wheel is rotated through the correct angle to move the next unused blister into alignment with the piercer during the opening stroke.

When the outer cover is rotated further during the second part of the opening stroke, drive to the indexing wheel remains disengaged while the ramp followers 122, 132 move along the flat sections 195*b*, 196*b* of their respective pierce ramps (stage V) until the outer cover reaches the fully open position. This second part of the stroke allows the blisters to be pierced while the indexing wheel is not being driven so that the blister strip is stationary, in the same manner as in WO 09/092652. In the fully open position (stage VI), the piercer has been inserted and the ramp followers 122, 132 are at the far ends of the flat sections of the pierce ramps 195*b*, 196*b*.

When the user closes the outer cover from the fully open position, the shuttle rotates back in the opposite direction. In the first part of the closing movement, the piercer is removed from the blister as the ramp followers 122, 132 move back along the flat sections of the pierce ramps 195b, 196b while the shuttle remains in the central, neutral position (stage VII).

At the start of the second part of the closing movement, the second angled engaging face 128b of the track follower 128 contacts the second angled engaging face 184b of the track formation 180 (stage VIII) and the ramp followers 122, 132 reach the start of the sloping sections 195a, 196a of the pierce ramps.

Further rotation of the outer cover, and hence the shuttle, causes the track follower 128 to ride along the angled engaging face 184b and move onto the second track 183. The shuttle translates in the opposite direction to Stage II (i.e. the same direction as in Stage IV), moving the drive dogs even further away from the spokes. The ramp follower 132 on the second shuttle part moves down the sloping section 196a of the pierce ramp 196 and the other ramp follower 122 moves clear of its pierce ramp 195. The indexing wheel 160 is not driven by the shuttle 110 while the track follower moves along the second track 183 (Stage IX), so that the blister strip is not indexed by the closing of the outer cover.

At the point when the track follower reaches the end of the track formation 180 (stage X), the ramp follower 132 on the second shuttle part comes into contact with the close ramp 197 on the second (rear) side of the housing. Further rotation of the outer cover, and hence the shuttle, causes the ramp follower 132 to ride up the sloping section 197a of the ramp 197. When the second ramp follower 132 reaches the top of the close ramp 197b, the shuttle has returned to the central, neutral position. At the same time, the ramp follower 122 on the first shuttle part comes into contact with the top 194b of the first close ramp 194. This contact prevents the shuttle from overshooting the central position. This is the end of the closing stroke (stage XI), in which the mechanism has returned to its initial, fully closed position.

Thus the shuttle is driven axially by the track formation, the track follower, the ramps and the ramp followers. This axial motion of the shuttle changes the engagement between the outer cover and the indexing wheel from drive during the first part of the opening stroke, into neutral during the second part of the opening stroke and the closing stroke.

FIGS. 8 to 13 show a second embodiment which indexes the blister strip on closing as well as on opening the cover.

Figure 8A:
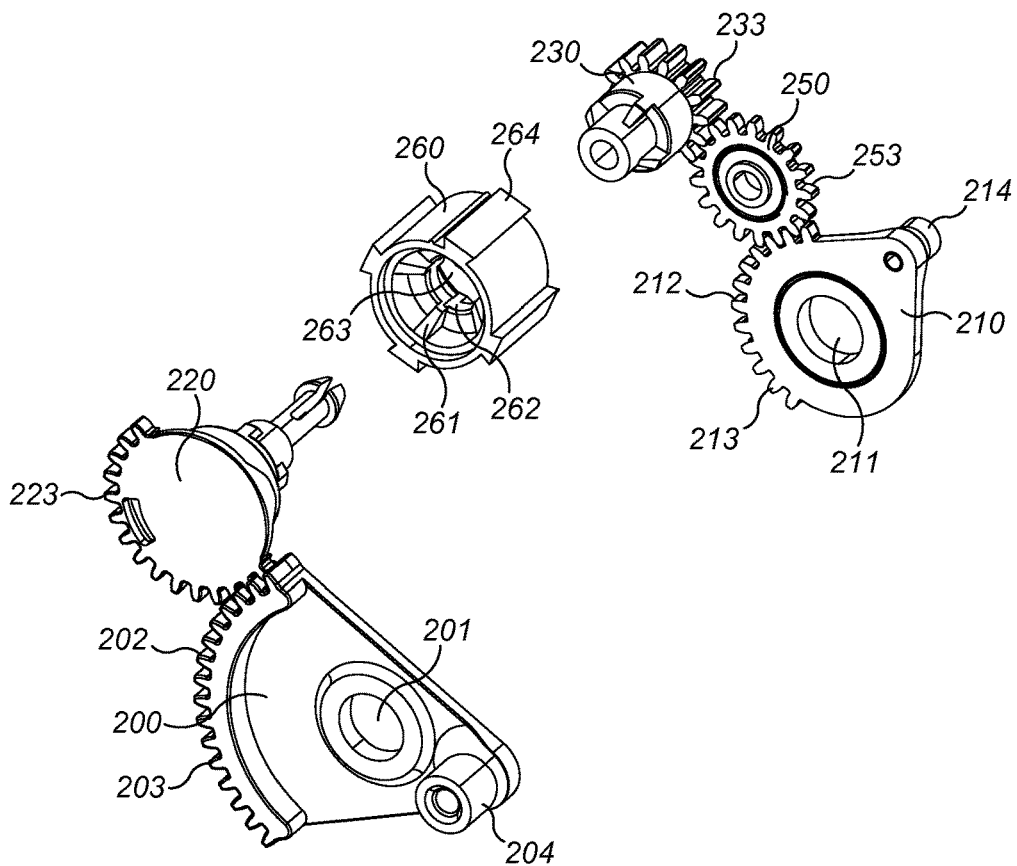
FIGS. 8A and 8B show expanded and assembled views of the indexing mechanism of a second embodiment.
Figure 8B:
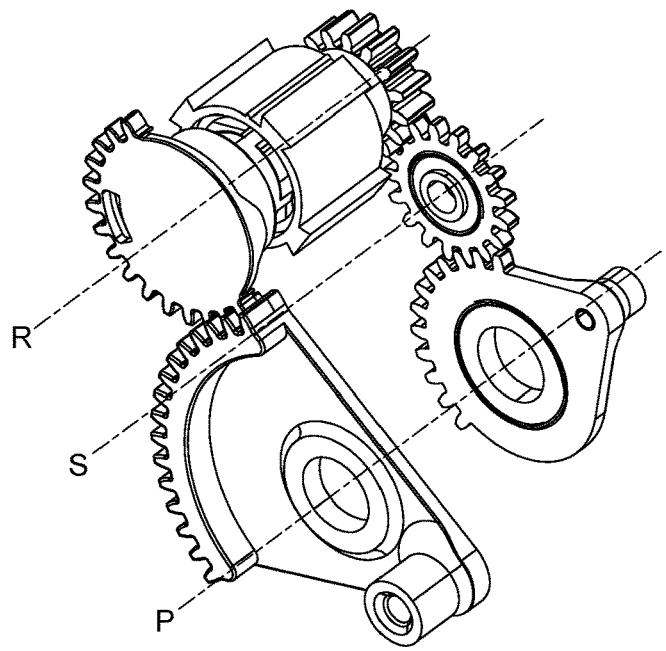

FIGS. 8A and 8B show expanded and assembled views of the indexing mechanism of the second embodiment. The mechanism is similar to that of the first embodiment, but has two sets of gears. As with the first embodiment, the gears engage and disengage with the indexing wheel by means of a shuttle.

The mechanism comprises a first (opening) actuator gear 200, a first shuttle part 220 which functions as a first drive gear, a blister strip indexing wheel 260, a second shuttle part 230 which functions as a second drive gear, an idler gear wheel 250 and a second (closing) actuator gear 210. The first and second actuator gears 200, 210 are formed as plate-like portions, each having a central pivot hole 201, 211 which fit onto the axles 7 (see FIG. 1) on either side of the housing, so that the actuator gears are mounted for rotation on the housing about the same axis P as the outer cover. The actuator gears 200, 210 have gear elements 202, 212 which consist of teeth 203, 213 extending around part of the periphery of each gear.

The first and second actuator gears 200, 210 may be keyed or otherwise attached to the outer cover when the inhaler is assembled so that the first and second actuator gears and the outer cover rotate together. For example, round posts 204, 214 protrude from the actuator gears 200, 210 and are received in corresponding holes 15 in each side of the outer cover (see FIG. 1). Opening or closing the outer cover thereby causes the actuator gears 200, 210 to rotate about axis P. Alternatively, the first and second actuator gears 200, 210 and outer cover may be formed as a single component, for example they may be moulded together as a unitary piece.

The first and second shuttle parts 220, 230 and the indexing wheel 260 are mounted for rotation about axis R. The indexing wheel 260 comprises a number of spokes 261 (typically four) extending from a hub 262 which surrounds a central circular recess 263. The spokes are arranged so that a blister locates between the protruding ends 264 of successive spokes as the blister strip passes around the indexing wheel.

The first actuator gear element 202 transmits drive from the outer cover as it is rotated to the first shuttle part 220 by means of the gear teeth 203 which mesh with corresponding gear teeth 223 on the first shuttle part 220. The second actuator gear element 212 transmits drive from the outer cover as it is rotated via the idler gear wheel 250 to the second shuttle part 230. The idler gear wheel is mounted for rotation on an idler gear axle 272 (shown in FIG. 12B) about axis S. The teeth 213 on the second actuator gear mesh with corresponding teeth 253 on the idler gear wheel 250 which in turn mesh with teeth 233 on the second shuttle part 230.

The first shuttle part 220 rotates in response to rotation of the first actuator gear 200, and the second shuttle part 230 rotates in response to rotation of the second actuator gear 210, but in the opposite sense, due to the presence of the idler gear wheel 250. Thus, in contrast to the first embodiment, the first and second shuttle parts are free to rotate independently of each other. The shuttle parts 220, 230 connect to and disconnect from the indexing wheel 260, in order to drive it to rotate and thereby index the blister strip.

Figure 9A:
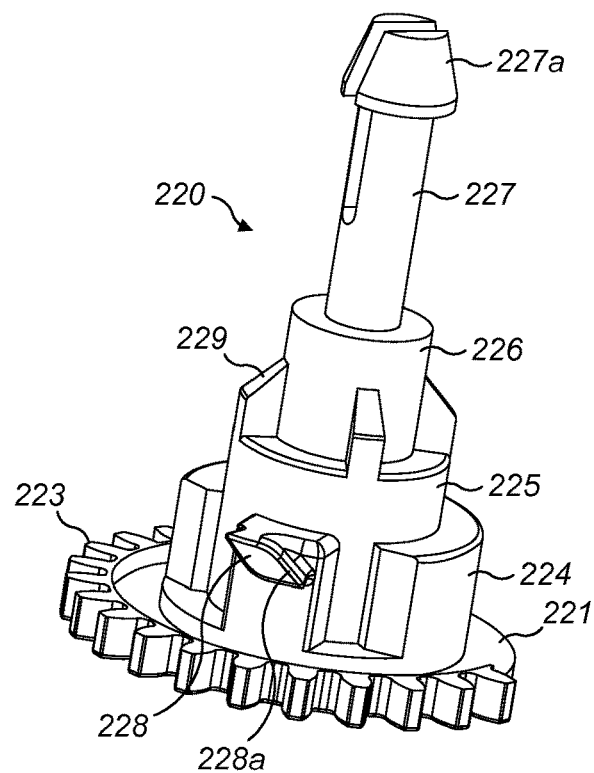
FIGS. 9A and 9B show perspective views of the first shuttle part.
Figure 9B:
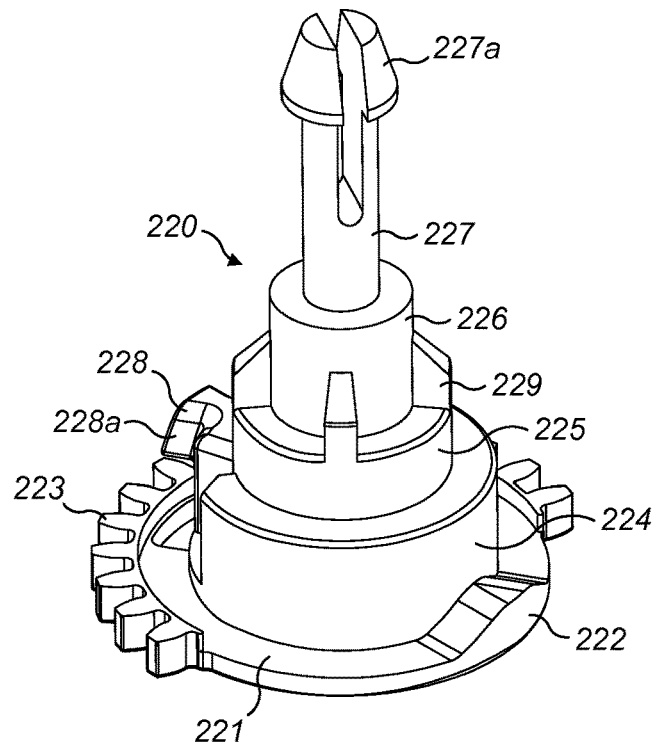
Figure 10A:
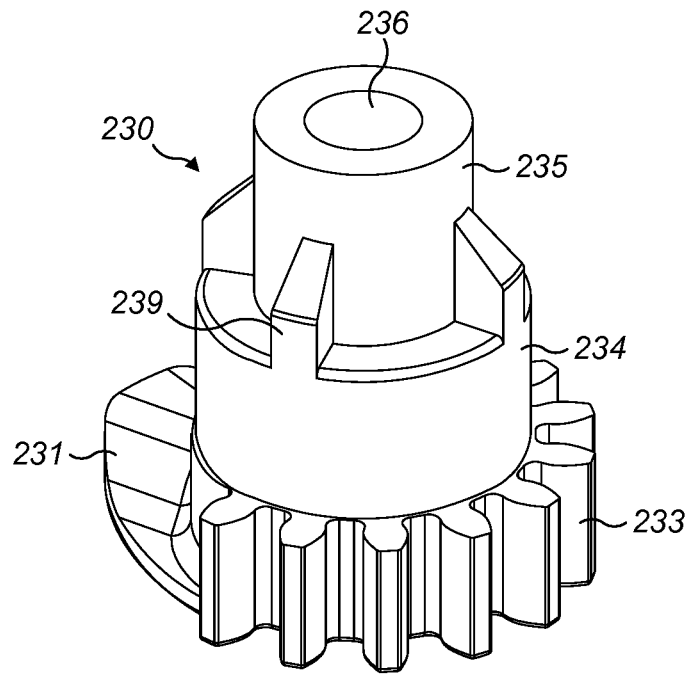
FIGS. 10A and 10B show perspective views of the second shuttle part.
Figure 10B:
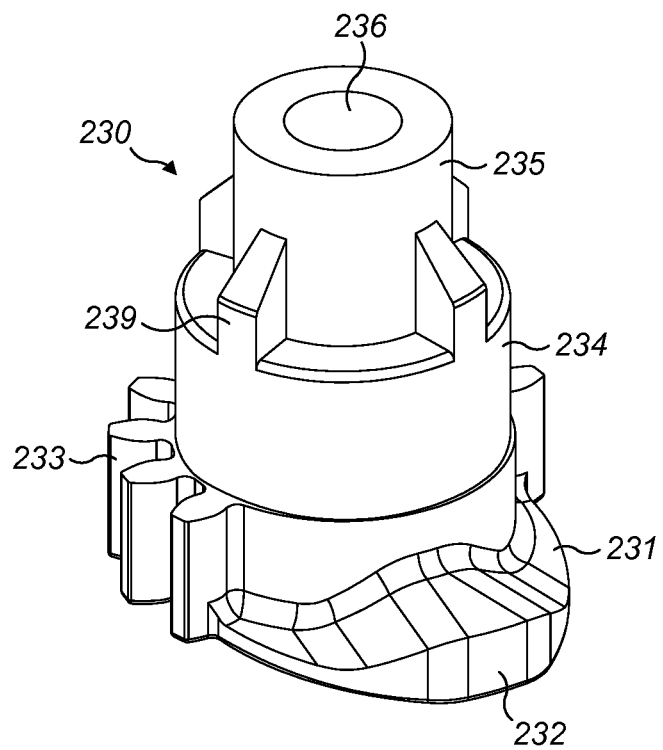
Figure 11:
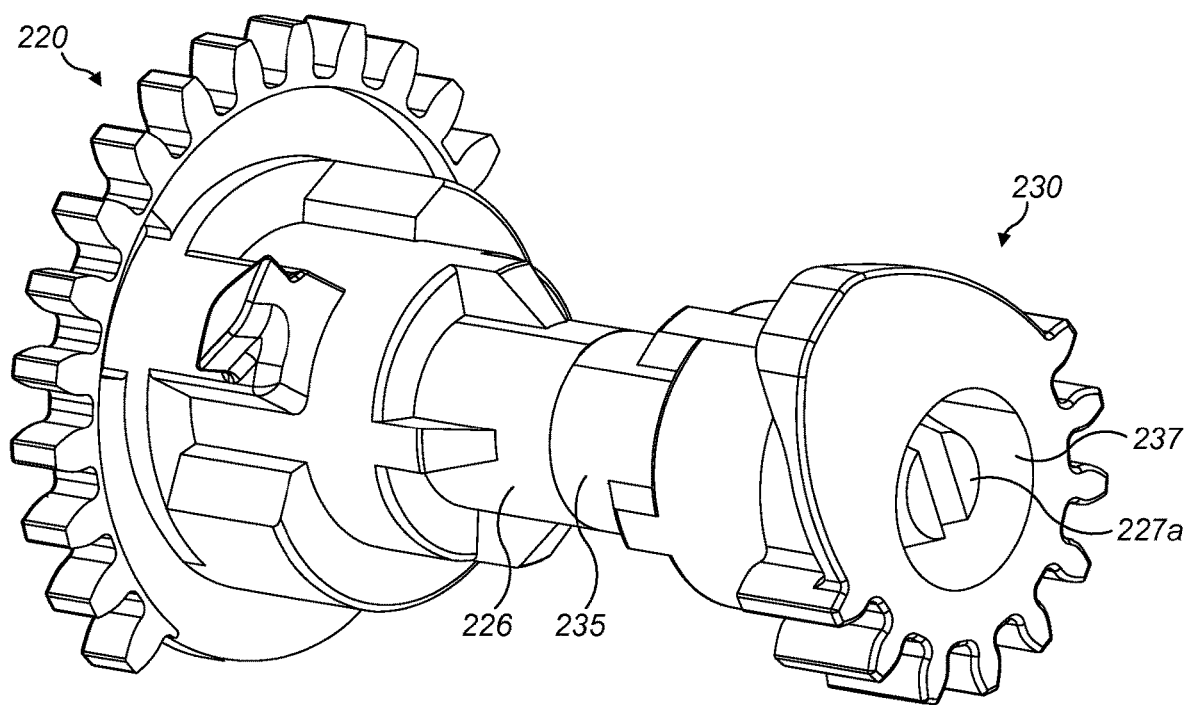
FIG. 11 shows a perspective view of the first and second shuttle parts connected together.

FIGS. 9A and 9B show perspective views from different positions of the first shuttle part 220. FIGS. 10A and 10B show similar views of the second shuttle part 230. FIG. 11 shows the first and second shuttle parts connected together to form the shuttle (the indexing wheel is not shown, so that features that would otherwise not be visible are apparent).

The first shuttle part 220 comprises a flange 221 having a small hump on one side which functions as a first ramp follower 222, and a shaft which extends axially from the centre of the flange 221. Gear teeth 223 protrude radially from the flange around about half of its circumference on the side opposite the hump. The shaft has first, second, third and fourth cylindrical sections 224, 225, 226, 227 having different radii. The first shaft section 224, which has the largest radius, is adjacent to the flange. The fourth shaft section 227, which is furthest from the flange, has the smallest radius. The second 225 and third 226 shaft sections lie between the first 224 and fourth 227 shaft sections, and have intermediate radii. A track follower 228 protrudes radially from close to the distal end of the first shaft section 224, on the side opposite the hump 222. Part of the first shaft section is cut away on either side of the track follower. The track follower 228 has first and second angled engaging faces 228a, 228b on its ends, so that it is rhomboid in shape (when viewed in the radial direction).

The second shuttle part 230 comprises a flange 231 also having a hump which functions as a second ramp follower 232, and an axial shaft. The shaft has first and second cylindrical sections 234, 235 with the same radii as the second 224 and third 225 shaft sections respectively of the first shuttle part 220. Gear teeth 233 protrude radially from the first shaft section around about half of its circumference on the side opposite the hump 232. A central circular hole 236 extends through the second shuttle part 230.

The fourth shaft section 227 of the first shuttle part has a radius which corresponds to that of the central circular hole 236 of the second shuttle part. A clip connection 227a is situated at the distal end of the fourth shaft section 227 and fits into a corresponding circular recess 237 at the distal end of the central circular hole 236 of the second shuttle part 230, as can be seen in FIG. 11.

FIG. 11 shows the second shuttle part 230 connected to and mounted for rotation on the fourth shaft section 227 of the first shuttle part 220. The clip connection 227a and corresponding recess 237 hold the first 220 and second 230 shuttle parts together in the axial direction. However, in contrast to the first embodiment, the shuttle parts are free to rotate independently of each other. The length of the fourth shaft section 227 (including the clip connection 227a) corresponds to the total thickness of the second shuttle part 230. Thus, when the fourth shaft section 227 is inserted into the central circular hole 236, the third shaft section 226 of the first shuttle part 220 abuts the second section 235 of the second shuttle part 230.

The radius of the third shaft section 226 of the first shuttle part and of the second section 235 of the second shuttle part correspond to that of the central circular recess 263 of the indexing wheel 260. These sections 226, 235 together form a bearing surface on which the indexing wheel 260 rotates, also on axis R.

Four equi-angularly spaced drive dogs 229, 239 protrude radially outwards from the third shaft section 226 of the first shuttle part and from the second section 235 of the second shuttle part respectively. The drive dogs 229 on the first shuttle part are formed as walls which extend axially from the second shaft section 225 along part of the third shaft section 226. Similarly, the drive dogs 239 on the second shuttle part are formed as walls which extend axially from the first section 234 along part of the second section 235.

The drive dogs engage and disengage with the spokes of the indexing wheel in a similar manner to the first embodiment. The axial ends of both the drive dogs and the spokes are sloped at an angle of 45°. This maximizes the contact area between the faces of the drive dogs and the spokes when they are engaged for the fixed axial engagement distance, which is limited by the distance that the shuttle translates, as before.

Figure 12A:
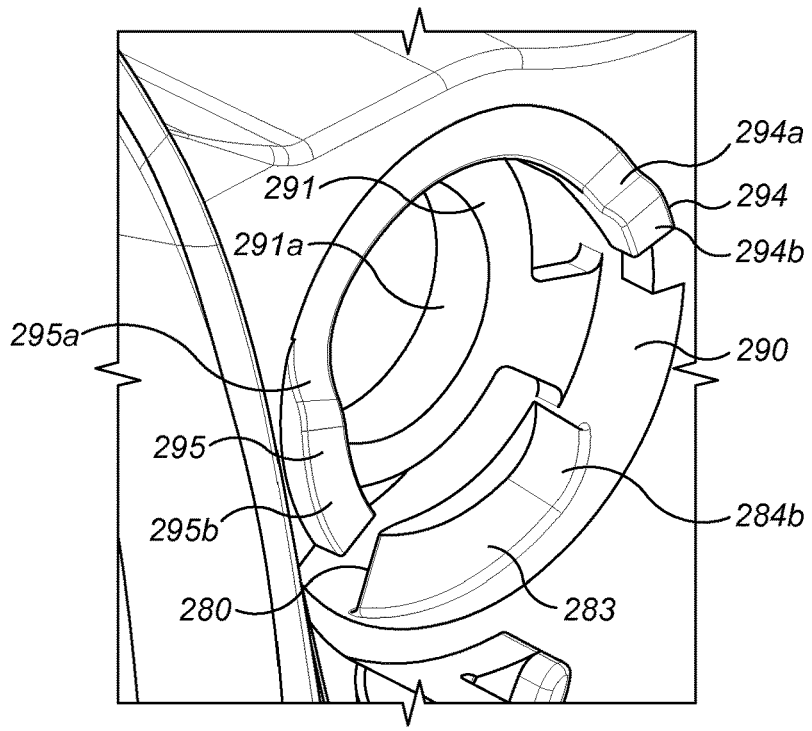
FIGS. 12A and 12B are perspective views of each side of the housing, showing the track formation and ramps.
Figure 12B:
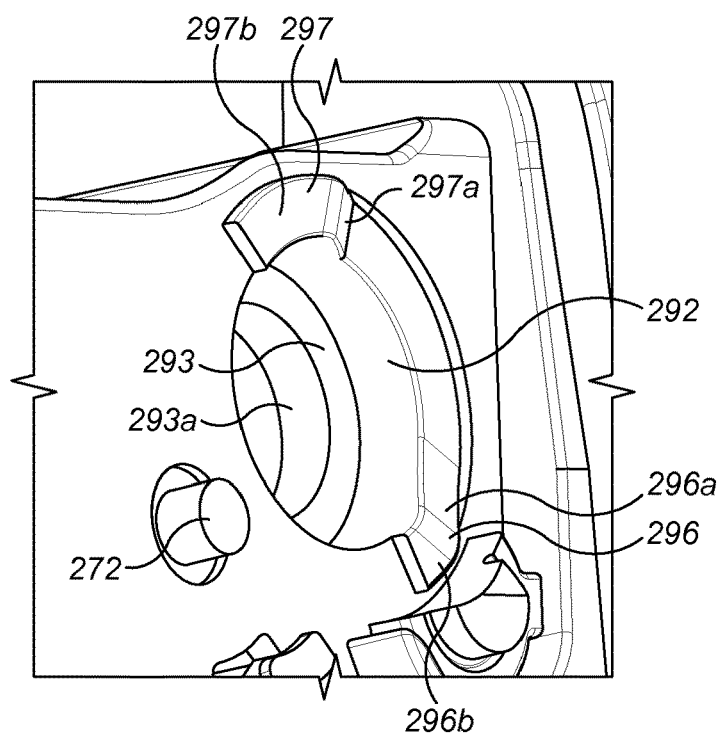
Figure 13A:
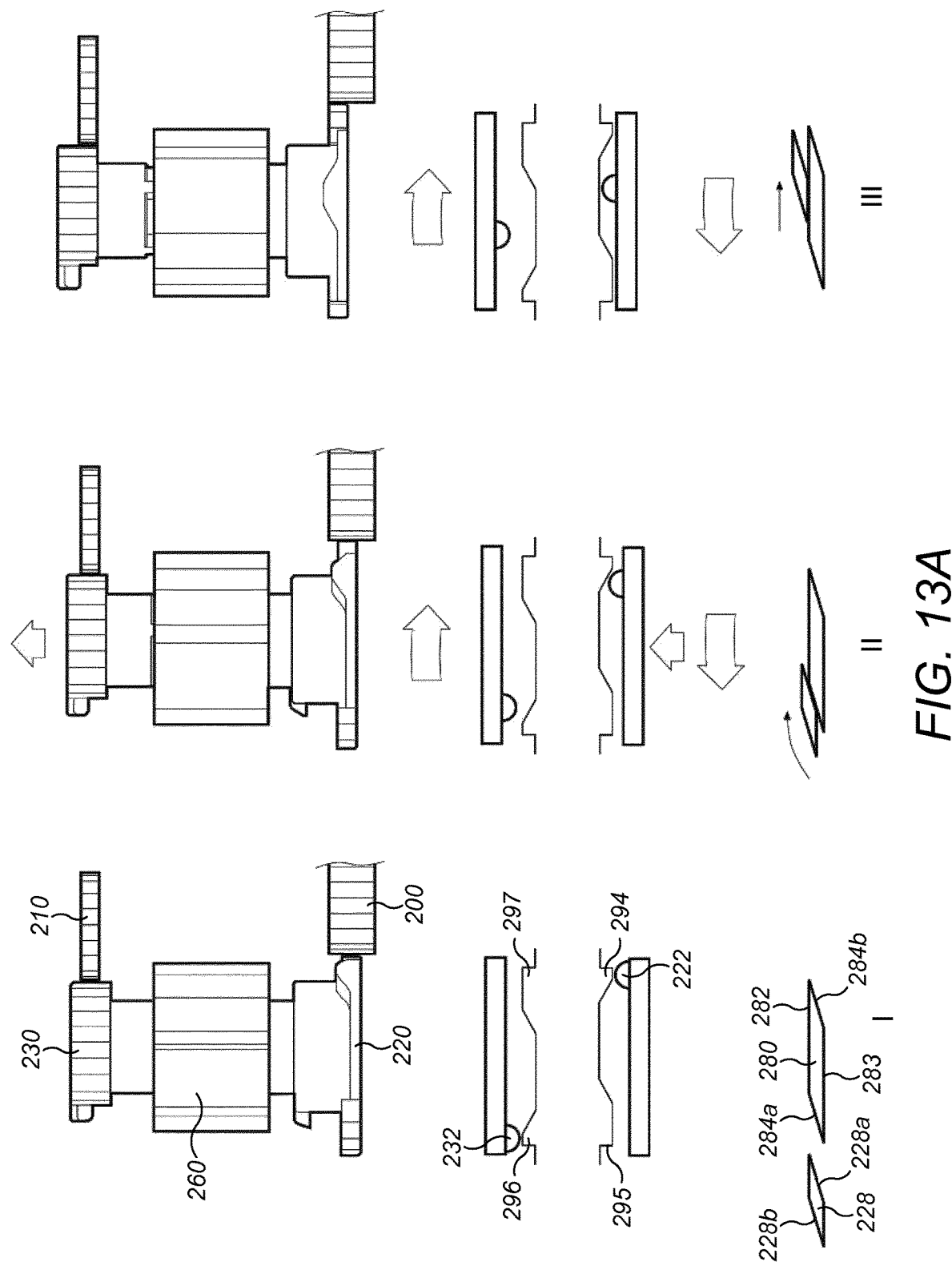
FIGS. 13A and 13B schematically show the positions of the shuttle and the indexing wheel (top row), the ramps and ramp followers (middle row) and the track follower and the track formation (bottom row) at several stages during opening and closing of the outer cover.
Figure 13A:
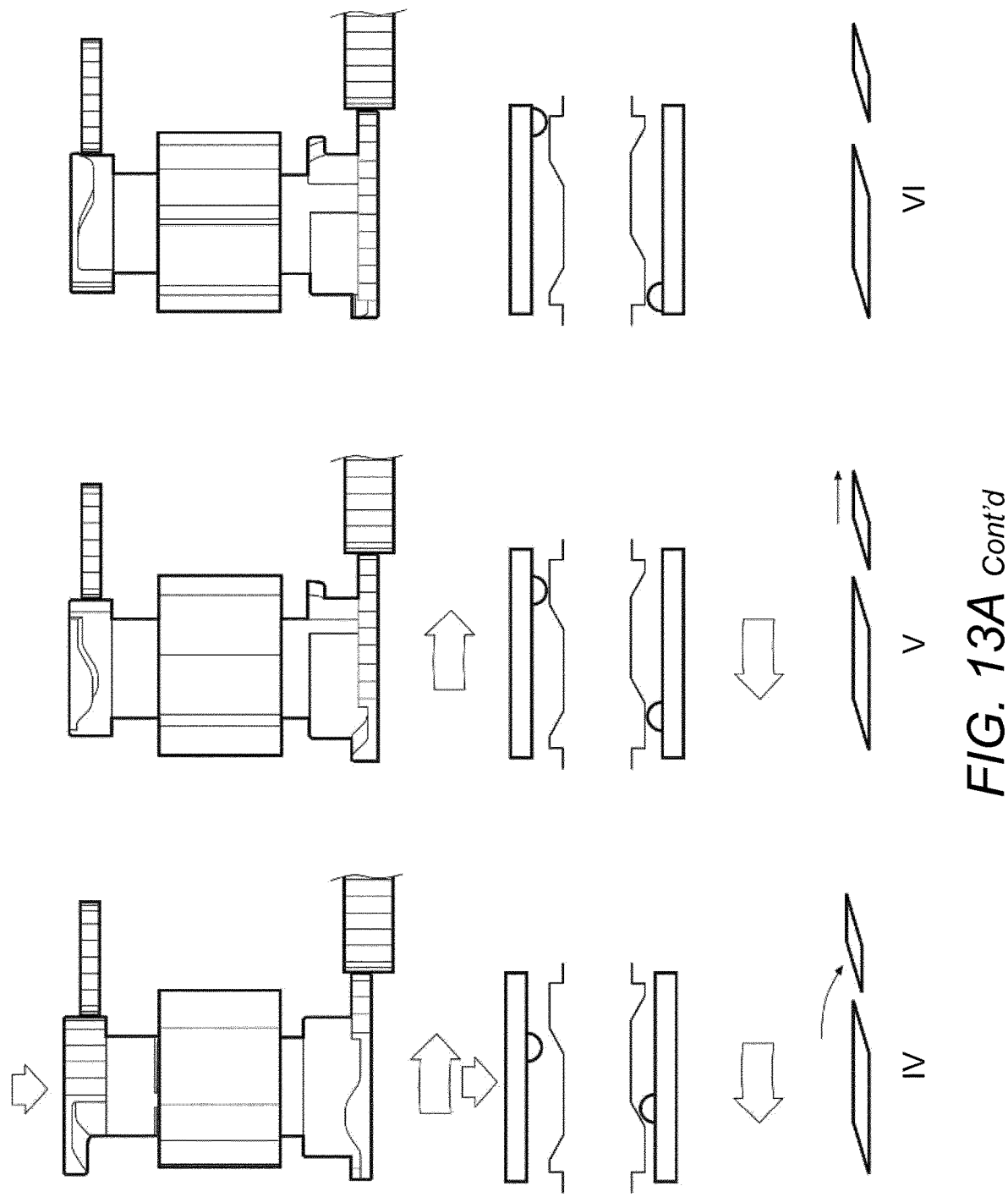
Figure 13B:
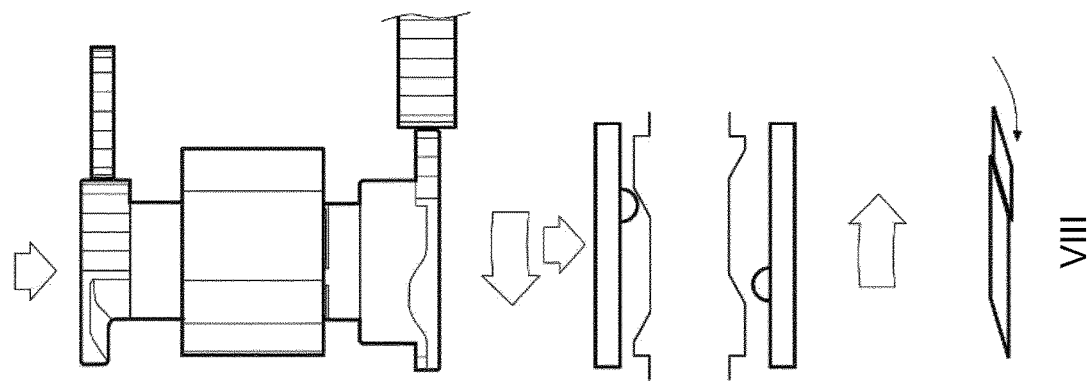
Figure 13B:
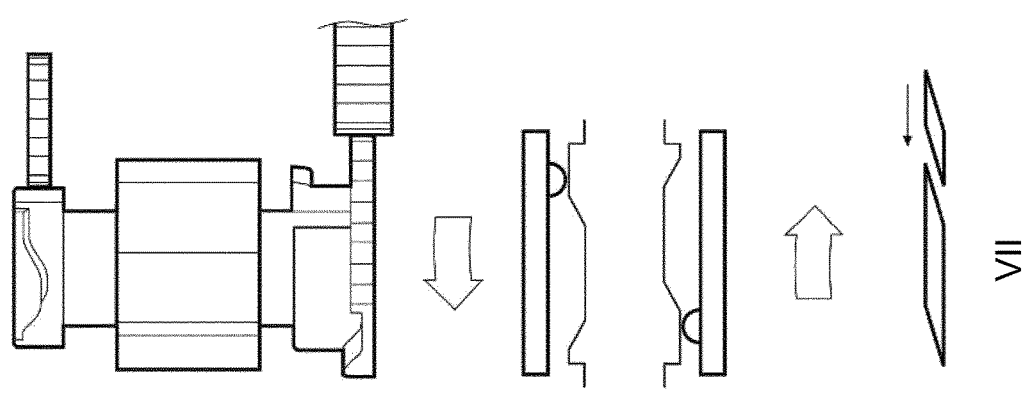
Figure 13B:
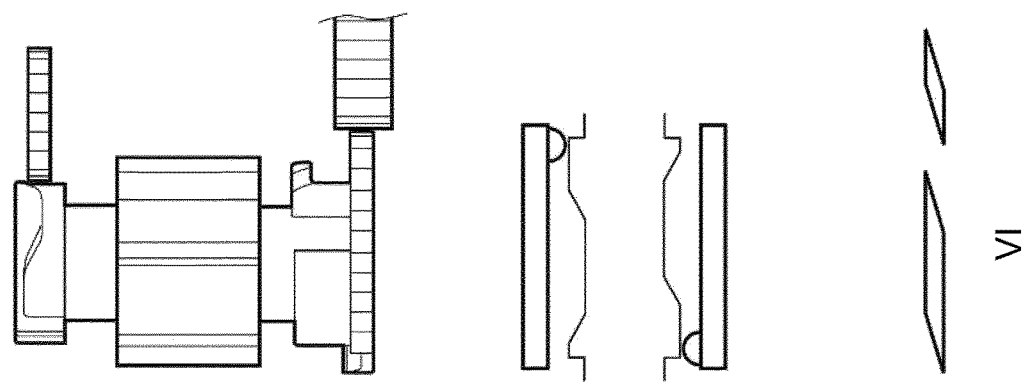
Figure 13B:
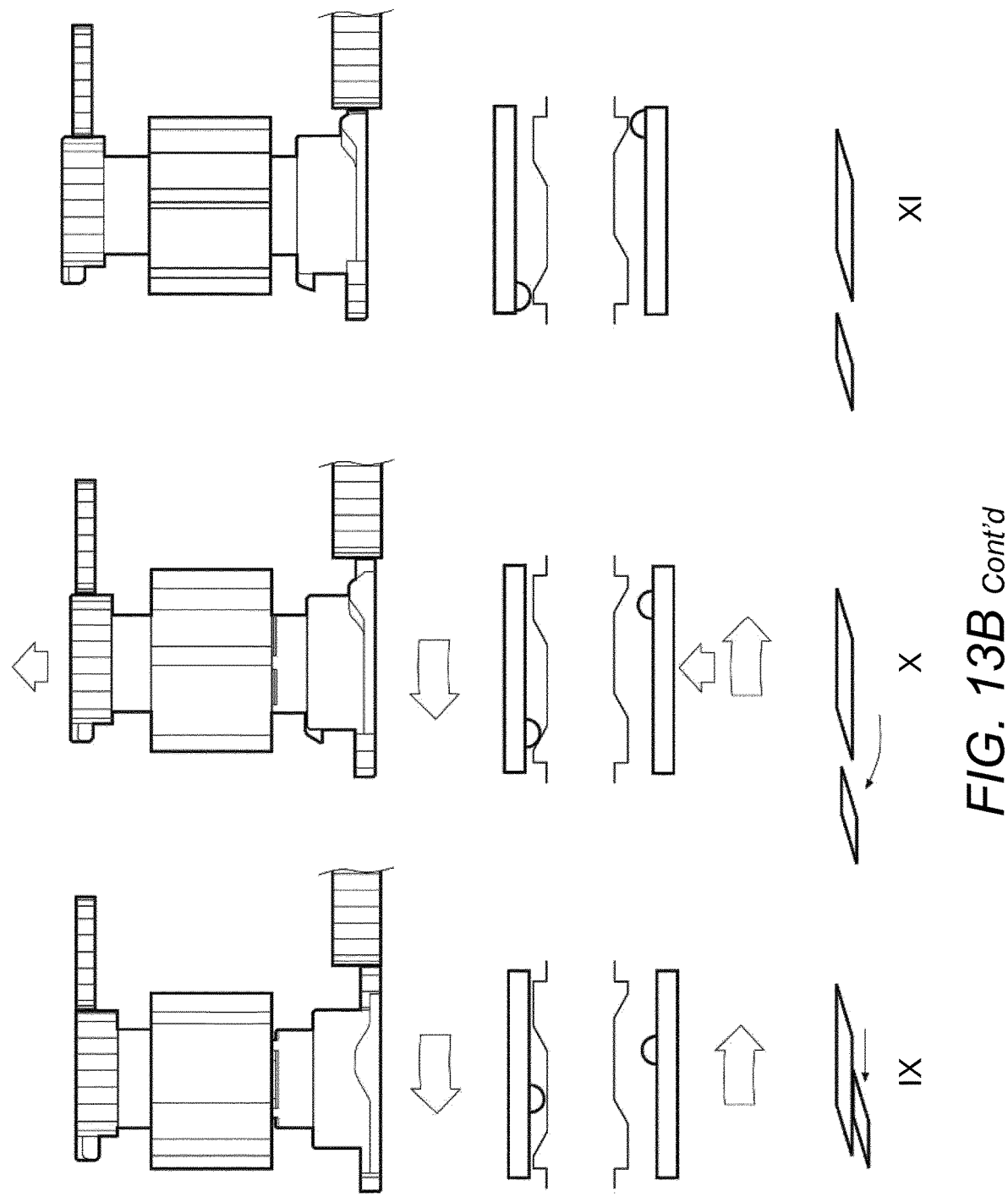

FIGS. 12A and 12B show close up views of the regions of the first (front) and second (rear) sides of the housing where the shuttle parts are located. The first side of the housing has a first circular recess 290 within which a first ring 291 is formed. Correspondingly, the second side of the housing has a second circular recess 292 a second ring 293. The radius of each ring 291, 293 corresponds to that of the second shaft section 225 of the first shuttle part and the first section 234 of the second shuttle part.

The radially inward surface 291a of the first ring 291 forms a bearing surface for the second shaft section 225 of the first shuttle part so that it is mounted for rotation on axis R. Similarly, the corresponding surface 293a of the second ring 293 forms a bearing surface for the first section 234 of the second shuttle part. The indexing wheel 260 is mounted for rotation about axis R on the bearing surface formed by the third shaft section 226 of the first shuttle part 220 and the second section 235 of the second shuttle part 230. At the same time, it is held in place axially in the housing between the inner axial faces of the rings 291, 293 (these faces are not visible in FIGS. 12A and 12B).

As shown in FIG. 12A, a track formation 280 protrudes from the first circular recess 290, in the form of a barrier which separates and defines first and second tracks 282, 283 on either side, in the same way as the first embodiment. The ends of the barrier have angled faces 284a, 284b. Two ramps, a short close ramp 294 and a long pierce ramp 295, protrude from the outer side of the housing adjacent to and on opposite sides of the circular recess 290.

The second side of the housing, shown in FIG. 12B, has similar close and pierce ramps 296, 297 but does not have a track formation. The ramps correspond in size and shape to ramps 294, 295 but are located at different angular positions around the circular recess 292. Compared to the first embodiment, the positions of the ramps 296, 297 are reversed, since in the second embodiment, the first and second shuttle parts rotate in opposite senses.

The shuttle is able to translate because the second shaft section 225 of the first shuttle part and the first section 234 of the second shuttle part can slide axially on their bearing surfaces 291a, 293a. The distance that the shuttle translates is equal to the width of the track formation 280 plus the width of the track follower 228.

Similar to the first embodiment, in order for the gear teeth 223, 233 on the first and second shuttle parts to remain engaged with the first actuator gear and the idler gear respectively, one gear of each pair is thicker. As shown for example in FIG. 8, the gear teeth 203, 233 of the first actuator gear 200 and the second shuttle part 230 are thicker (axially) than the gear teeth 223, 253 of the first shuttle part 220 and the idler gear 250 (however, the thicker and thinner teeth could equally be the other way around). In order to ensure that the gears are fully engaged in both drive positions, the thickness of the thicker gears is thickness of the thin gear plus the distance that the shuttle translates.

FIG. 13 shows the positions of the actuator gears 200, 210, the shuttle parts 220, 230 and the indexing wheel 260 (top row), the ramps 294, 295, 296, 297 and ramp followers 222, 232 (middle row) and the track follower 228 and track formation 280 (bottom row) at several stages during opening (FIG. 13A) and closing (FIG. 13B) of the outer cover. The track follower and ramp followers each move in a circular arc as the gears are rotated, but in FIG. 13, the motion is schematically shown as being linear for simplicity.

In stage I, the outer cover is in the closed position. The shuttle is located centrally with respect to the indexing wheel and the mechanism is in neutral. Stages II, III and IV correspond to the first part of the opening stroke. The shuttle moves axially relative to the indexing wheel in a manner that is described in detail below, so that the drive dogs on the first shuttle part engage with the spokes of the indexing wheel. Stage V is the second part of the opening stroke in which the first shuttle part disengages from the indexing wheel and the mechanism is in neutral whilst the piercer is inserted. In stage VI, the outer cover is in the fully open position. Stage VII is the first part of the closing stroke in which the mechanism is in neutral whilst the piercing elements are removed. Stages VIII, IX and X correspond to the second part of the closing stroke. The shuttle moves axially in the opposite direction, so that the drive dogs on the second shuttle part engage with the spokes of the indexing wheel. Finally, at the end of the closing stroke (stage XI), the shuttle returns to the central position and the cover is in the fully closed position, i.e. the same configuration as stage I.

The mechanism operates as follows. When the outer case is in the closed position (stage I), the drive dogs 229, 239 on both the first and second 220, 230 shuttle parts are spaced apart from the spokes 261 of the indexing wheel 260. The track follower 228 on the first shuttle part 220 is spaced apart from the track formation 280. The ramp followers 222, 232 sit on the tops of their respective close (short) ramps 294, 296.

When the user opens the outer cover, the gears rotate. The track follower 228 moves towards the track formation 280, so that the first angled engaging face 228a on the track follower comes into contact with the first angled engaging face 284a of the track formation 280. The track follower 228 rides up the angled engaging face 284a (stage II) to one side 282 of the track formation. This pushes the first shuttle part 220 towards the indexing wheel 260. At the same time, the ramp follower 222 on the first shuttle part moves along the sloping section 294a of the first close ramp 294. The second shuttle part (which is connected to the first shuttle part by the clip connection 227a) correspondingly moves away from the indexing wheel and its ramp follower 232 moves clear of its close ramp 296. As the first shuttle part moves towards the indexing wheel 260, the drive dogs 229 engage the spokes 261. Consequently, as the track follower 228 moves along the first track 282 (stage III), the first shuttle part 220 drives the indexing wheel 260 to rotate.

At the point when the track follower 228 reaches the end of the track formation 280 (stage IV), the ramp follower 222 on the first shuttle part comes into contact with its long ramp 295. Further rotation of the outer cover, and hence the shuttle parts, causes the ramp follower 222 to ride up the sloped section 295a of the pierce ramp 295. This pulls the first shuttle part away from the indexing wheel so that the drive dogs 229 disengage from the spokes 261. At the same time, the second shuttle part 230 moves back towards the indexing wheel. The first ramp follower 222 reaches the flat section of the pierce ramp 295b, at which point the shuttle has returned to the central, neutral position. The ramp follower 232 on the second shuttle part also comes into contact with the flat section 297b of the pierce ramp 297 on the second (rear) side of the housing. This contact prevents the shuttle from overshooting the central position. This is the end of the first part of the opening stroke.

As with the first embodiment, the length of the track formation 280 controls the extent of rotation of the indexing wheel 260 relative to the extent of rotation of the shuttle parts 220, 230. Where two blisters are indexed and pierced on each actuation, the track length is preferably chosen so that the indexing wheel is rotated through the correct angle to move the next, unused blister, into alignment with the blister piercing element during the opening stroke and another during the closing stroke.

When the outer cover is rotated further during the second part of the opening stroke (stage V), drive to the indexing wheel is disengaged while the ramp followers 222, 232 move along the flat sections 295b, 297b of their respective pierce ramps until the outer cover reaches the fully open position. This second part of the stroke allows the blisters to be pierced while the indexing wheel is not being driven and the blister strip is stationary, as with the first embodiment. In the fully open position (stage VI), the piercer has been inserted and the ramp followers 222, 232 are at the far ends of the flat sections of the pierce ramps 295b, 297b.

When the user closes the outer cover from the fully open position, the shuttle parts rotate in the reverse directions. In the first part of the closing movement, the piercer is removed from the blisters and the ramp followers 222, 232 move back along the flat sections of the pierce ramps 295b, 297b while the shuttle remains in the central, neutral position (stage VII).

At the start of the second part of the closing movement, the second angled engaging face 228b of the track follower 228 contacts the second angled engaging face 284b of the track formation 280 (stage VIII) and the ramp followers 222, 232 reach the sloping sections 295a, 297a of the pierce ramps.

Further rotation of the outer cover, and hence the shuttle parts, causes the track follower 228 to ride along the angled engaging face 284b and move onto the second track 283. The first shuttle part moves away from, and the second shuttle part moves towards, the indexing wheel. The ramp follower 232 on the second shuttle part moves down the sloping section 297a of the pierce ramp 297. The other ramp follower 222 moves clear of its pierce ramp 295. As the second shuttle part moves inwards, its drive dogs 239 engage the spokes 261 of the indexing wheel 260. The indexing wheel 260 is now driven by the second shuttle part 230 while the track follower moves along the second track 283 (stage IX). Since the second shuttle part rotates in the opposite sense to the first shuttle part due to the idler gear, the blister strip is indexed forwards (not backwards) by the closing of the outer cover.

At the point when the track follower reaches the end of the track formation 280 (stage X), the ramp follower 232 on the second shuttle part comes into contact with the close ramp 296 on the second (rear) side of the housing. Further rotation of the outer cover, and hence the shuttle parts causes the ramp follower 232 to ride up the sloped section 296a. This pulls the second shuttle part outwards so that the drive dogs 239 disengage from the spokes 261 of the indexing wheel, while the first shuttle part is pulled inwards.

The second ramp follower 232 reaches the top of the close ramp 296b, at which point the shuttle has returned to the central, neutral position (stage XI). At the same time, the ramp follower 222 on the first shuttle part comes into contact with the top 294b of the first close ramp 294, which prevents the shuttle from overshooting the central position. This is the end of the closing stroke, and the mechanism has returned to its initial, fully closed position.

Thus, the linked shuttle parts together form the shuttle, which is driven axially by the track formation, the track follower, the ramps and the ramp followers. The motion of the shuttle changes the gearing between the outer cover and the indexing wheel from drive during the first part of the opening stroke, into neutral during the second part of the opening stroke and the first part of the closing stroke, and then into drive again during the second part of closing. The blister strip is indexed forwards during both opening and closing, so that two blisters are indexed on each full opening and closing cycle.

The inhaler of this embodiment allows the contents of two blisters to be dispensed on each actuation, for example from a blister strip that contains two or more different medicaments or formulations. Alternatively, each blister could contain the same formulation, so that the inhaler provides a double dose. Of course, the piercer is configured to pierce two blisters simultaneously, e.g. by having two sets of piercing elements, one for each blister.

Figure 14:
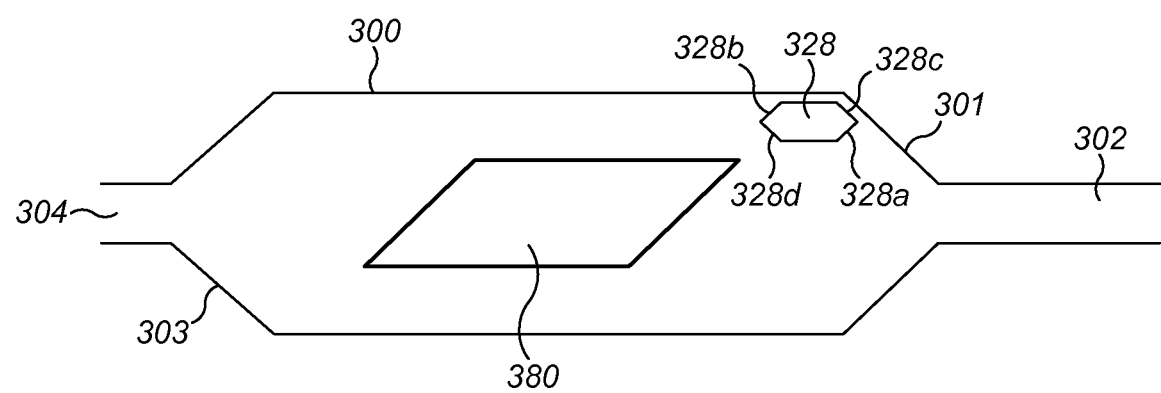
FIG. 14 schematically shows an alternative form of the track formation.

In either of the above embodiments, at the end of the opening and closing strokes the shuttle could be returned to its central, neutral position in a different manner. In this alternative embodiment, the ramps and ramp followers are removed, and instead an outer wall 300 is added to the track formation, as shown schematically in FIG. 14. The track follower 328 has two angled engaging faces at each end 328a, 328c and 328b, 328d respectively, i.e. it is hexagonal instead of rhomboid. In this case, shortly after the track follower 328 passes the end of the central barrier 380, it comes into contact with the angled part 301 of the outer wall. The additional angled engaging face 328c is parallel to the angled part of the outer wall 301. This contact guides the track follower along the angled part 301 so that the shuttle returns to the central position. Then the track follower moves along the central straight section 302 in the second part of the opening stroke, during which piercing takes place. Similarly, in the second part of the closing stroke, the angled engaging face 328d contacts the angled part 303 of the outer wall at the other end of the track formation. The track follower 328 is guided back to the central position and then moves along the short straight section 304 which corresponds to the end of the closing stroke. Thus, in comparison to the embodiments described above, the angled parts 301, 303 serve the same function as the angled sections of the pierce and close ramps. Similarly, the straight sections 302, 304 serve the same function as the flat sections of the pierce and close ramps. The track follower additionally performs the function of the ramp followers.

The shuttle mechanism of the invention has a number of advantages.

Firstly, the mechanism is in a stable, neutral configuration when the outer cover is in the closed position. None of the components is under stress in this position. Furthermore, if an external force is applied to the device, for example by dropping it, the mechanism remains in neutral and cannot be accidentally forced into a drive position.

Secondly, actuation of the inhaler is reversible during the first part of the opening stroke, up to the point at which the track follower passes the end of the track formation. The user can abort actuation simply by closing the outer cover, which moves the blister strip back to its previous position. Moreover, in the second embodiment, the closing stroke is reversible through both the first part when the piercing elements are removed and through most of the second part during which the blister strip is indexed, i.e. up to the point at which the track follower passes the other end of the track formation. Thus, for example, if the user accidentally begins to close the outer case without having inhaled, they can simply open it again, inhale and then close as normal.

Thirdly, unlike WO 09/092652, there are no flexible portions that are deflected to cause engagement with the indexing wheel. Instead, the shuttle translates axially with respect to the indexing wheel so that the drive dogs engage with its spokes. The absence of flexible parts has the advantage that the mechanism is robust and simple to manufacture.

Instead of causing indexing and piercing, the outer cover could alternatively be passive, so that opening and closing it exposes and covers the mouthpiece, but does not actuate the device. In this case, the inhaler includes a separate actuating lever which may be revealed when the outer cover is rotated out of its closed position. The lever may have a protruding button to facilitate actuation by the user, as described in WO 13/175176. The actuating lever is connected to the actuator gear(s) in an analogous manner to the outer cover in the embodiments described above. Thus in this variant, the actuating lever (instead of the outer cover) is keyed or otherwise attached to the actuator gear(s). The outer cover and actuating lever may also include cooperating means configured so that, after inhalation, when the user rotates the outer cover back into its closed position, the actuating lever is also rotated back into its initial position. In other words, the outer cover is passive during opening, but is linked to the actuating lever during closing.

Instead of the indexing mechanism being disengaged before piercing, it could be configured to disengage after the piercer has begun to pierce the lid of a blister so that the piercer is drawn across the lid of the blister as it enters. This creates a larger opening than that created when the strip is stationary during piercing, which can help to ensure that the drug dose is entrained in the airflow and removed from the blister.

Other opening means may be used instead of a piercer; for example the blisters may be opened by peeling the lid from the base, or by folding the blister so that the lid is burst open, as described in WO 16/083102.

The blister strip preferably has numbers printed on it that are visible to the user, for example through a window in the housing, in order to display the number of remaining (or used) doses. This is preferable to having a separate dose counter, because there is no possibility of the incorrect dose number being displayed.

In addition to the airflow through the blisters, the inhaler may also have one or more bypass airflow channels. Air flows through the bypass channel from outside the device and into the mouthpiece, without passing through the blister. The bypass airflow reduces the resistance of the device. The size of the bypass is chosen so that sufficient air nonetheless flows through the blisters to ensure complete evacuation of the powder.

Preferably the inhaler retains the used blisters. More preferably the inhaler has a wall to separate the interior of the housing into used and unused blister compartments. The wall is preferably rigid and slideably mounted so that the sizes of the unused and used blister compartments change relative to each other as the number of blisters that are used increases and the number of unused blisters decreases.

The used blisters are preferably crushed so that they take up less space. Thus the blister strip indexing wheel is preferably positioned such that the distance between the hub and the inner surface of the housing is less than the depth of a blister so that onward rotation of the wheel after piercing causes a blister to be at least partially squashed between the hub and the wall.

The inhaler may be either passive or active. In a passive inhaler, the dose is entrained in a flow of air caused when the user inhales through the mouthpiece. An active inhaler includes means for generating a pressurized flow of gas or air through the blister to entrain the dose and carry it out of the blister through the mouthpiece and into the user's airway. Although the term "mouthpiece" is used, the invention is also applicable to devices in which the dose is inhaled through the nasal passages.

The invention claimed is:

1. An inhaler comprising:
a housing which contains a blister strip having a plurality of blisters which contain powdered medicament for inhalation,
a mouthpiece through which the medicament is inhaled by a user,
an indexing wheel for indexing the blister strip and an opening mechanism for opening the blisters,
an actuator which is movable between a first position and a second position in order to operate the indexing wheel and the opening mechanism,
a coupling mechanism for coupling the actuator to the indexing wheel so that the indexing wheel rotates together with the actuator during part of the motion of the actuator, characterized in that the coupling mechanism comprises a non-flexible shuttle that rotates on the same axis as the indexing wheel, and the entire shuttle translates along said axis axially relative to, the indexing wheel.

2. An inhaler according to claim 1, wherein the shuttle has a track follower which interacts with a track formation on the housing to cause the shuttle to translate axially so that it engages with the indexing wheel during a first part of the motion of the actuator.

3. An inhaler according to claim 1, wherein the shuttle comprises a first shuttle part and a second shuttle part.

4. An inhaler according to claim 3, wherein each shuttle part has a ramp follower which interacts with ramps on the housing to cause the shuttle to translate axially so that it disengages from the indexing wheel during a second part of the motion of the actuator.

5. An inhaler according to claim 3, wherein the first and second shuttle parts together form a bearing surface on which the indexing wheel is mounted for rotation.

6. An inhaler according to claim 3, wherein the blister strip is stationary during motion of the actuator from the second position back to the first position.

7. An inhaler according to claim 6, comprising an actuator gear which is connected to and driven by the actuator, wherein the actuator gear drives the first shuttle part, and wherein the first and second shuttle parts are connected so that rotation of the first shuttle part causes the second shuttle part to rotate.

8. An inhaler according to claim 3, wherein the blister strip is indexed forwards during motion of the actuator from the second position to the first position.

9. An inhaler according to claim 8 comprising first and second actuator gears which are connected to and driven by the actuator, and an idler gear, wherein the first and second shuttle parts are axially linked together whilst being free to rotate independently of each other and wherein the first actuator gear drives the first shuttle part, and the second actuator gear drives the idler gear which in turn drives the second shuttle part, so that the first and second shuttle parts rotate in opposite senses during motion of the actuator.

10. An inhaler according to claim 9 wherein the first shuttle part drives the indexing wheel during at least part of a forward motion of the actuator from the first position to the second position, and does not drive the indexing wheel during a reverse motion of the actuator from the second position to the first position; and the second shuttle part drives the indexing wheel during at least part of the reverse motion of the actuator, and does not drive the indexing wheel during the forward motion of the actuator.

11. An inhaler according to claim 8, wherein the blister strip is indexed by one blister during the motion of the actuator from the first position to the second position and by another blister during the motion of the actuator from the second position to the first position, so that two blisters are indexed and opened each time the actuator is moved from the first position to the second position and back.

12. An inhaler according to claim 11, wherein the two blisters contain different medicaments.

13. An inhaler according to claim 1, wherein the opening mechanism comprises a piercer and wherein the indexing wheel indexes the blister strip during a first part of the motion of the actuator from the first position to the second position, and wherein the piercer pierces one or more aligned blisters during a second part of the motion of the actuator from the first position to the second position.

14. An inhaler according to claim 1, wherein the inhaler has an outer cover which is pivotally mounted on the housing.

15. An inhaler according to claim 14, wherein the outer cover forms the actuator, wherein in the first position the outer cover is closed so that the mouthpiece is covered, and in the second position the outer cover is open so that the mouthpiece is exposed.

16. An inhaler according to claim 1, wherein the inhaler has a lever which forms the actuator so that motion of the lever causes indexing of the blister strip and opening of the blisters.

* * * * *